(12) United States Patent
Albitar et al.

(10) Patent No.: US 8,097,468 B2
(45) Date of Patent: Jan. 17, 2012

(54) USING PLASMA PROTEOMIC PATTERN FOR DIAGNOSIS, CLASSIFICATION, PREDICTION OF RESPONSE TO THERAPY AND CLINICAL BEHAVIOR, STRATIFICATION OF THERAPY, AND MONITORING DISEASE IN HEMATOLOGIC MALIGNANCIES

(75) Inventors: Maher Albitar, Coto de Caza, CA (US); Elihu H. Estey, Houston, TX (US); Hagop M. Kantarjian, Bellaire, TX (US); Francis J. Giles, Bellaire, TX (US); Michael J. Keating, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 12/582,998

(22) Filed: Oct. 21, 2009

(65) Prior Publication Data

US 2010/0063747 A1 Mar. 11, 2010

Related U.S. Application Data

(62) Division of application No. 11/110,374, filed on Apr. 20, 2005, now Pat. No. 7,622,306.

(60) Provisional application No. 60/563,873, filed on Apr. 20, 2004.

(51) Int. Cl.
*G01N 24/00* (2006.01)
*G01N 1/00* (2006.01)
*G01N 1/10* (2006.01)
*G01N 33/00* (2006.01)
*G01N 33/48* (2006.01)
*A61K 49/00* (2006.01)
*A61K 31/00* (2006.01)
*A01N 61/00* (2006.01)

(52) U.S. Cl. ............. 436/173; 436/63; 436/64; 436/86; 436/174; 436/179; 424/9.1; 424/9.2; 514/1

(58) Field of Classification Search .................. 424/9.1, 424/9.2; 436/63, 64, 86, 173, 174, 179; 514/1
See application file for complete search history.

(56) References Cited

U.S. PATENT DOCUMENTS

| 2004/0005634 A1 | 1/2004 | Patz, Jr. et al. ................. 435/7.1 |
| 2004/0029194 A1 | 2/2004 | Parish et al. .................. 435/7.23 |

FOREIGN PATENT DOCUMENTS

| EP | 1 083 181 | 3/2001 |
| WO | WO 02/06829 | 1/2002 |
| WO | WO 2004/029575 | 4/2004 |

OTHER PUBLICATIONS

Japanese Office Action, issued in Japanese counterpart Application No. 2007-509551, dispatch date Jun. 28, 2010.

Golub et al., "Molecular classification of cancer: class discovery and class prediction by gene expression monitoring," *Science*, 286:531-537, 1999.
Albitar et al., "Proteomic-based prediction of response to therapy in acute myeloid leukemia," *Blood*, 102(11):608a, 2003.
Anderson and Anderson, "The human plasma proteome," *Molec. Cell. Proteom.*, 1(11):845-867, 2002.
Cortes et al., "A randomized trial of liposomal daunorubicin and cytarabine versus liposomal daunorubicin and topotecan with or without thalidomide as initial therapy for patients with poor prognosis acute myelogenous leukemia or myelodysplastic syndrome," *Cancer*, 97 (5): 1234-1241, 2003.
Extermann et al., "Relationship between cleaved L-selectin levels and the outcome of acute myeloid leukemia," *Blood*, 92(9):3115-3122, 1998.
Ferrajoli et al., "The clinical significance or tumor necrosis factor-alpha plasma level in patients having chronic lymphocytic leukemia," *Blood*, 100(4):1215-1219, 2002.
Hanash et al., "Identification of a cellular polypeptide that distinguishes between acute lymphoblastic leukemia in infants and in older children," *Blood*, 73(2):527-532, 1989.
Hanash et al., "Lineage-related polypeptide markers in acute lymphoblastic leukemia detected by two-dimensional gel electrophoresis," *Proc. Natl. Acad. Sci. USA*, 83(3):807-811, 1986.
Hanenberg et al., "Expression of the CEA gene family members NCA-50/90 and NCA-160 (CD66) in childhood acute lymphoblastic leukemias (ALLs) and in cell lines of B-cell origin," *Leukemia*, 8(12):2127-2133, 1994.
Hayes et al., "Circulating HER-2/erbB-2/c-neu (HER-2) extracellular domain as a prognostic factor in patients with metastatic breast cancer: Cancer and Leukemia Group B Study 8662," *Clin. Cancer Res.*, 7(9):2703-2711, 2001.
Ito et al., "Elevated plasma level of differentiation inhibitory factor nm23-H1 protein correlates with risk factors for myelodysplastic syndrome," *Leukemia*, 16(2):165-169, 2002.

(Continued)

*Primary Examiner* — Alana Harris Dent
(74) *Attorney, Agent, or Firm* — Fulbright & Jaworski LLP

(57) ABSTRACT

The present invention demonstrates that the diagnosis and prediction of clinical behavior in patients with hematologic malignancies, such as leukemia, can be accomplished by analysis of proteins present in a plasma sample. Thus, in particular embodiments the present invention uses plasma to create a diagnostic or prognostic protein profile of a hematologic malignancy comprising collecting plasma samples from a population of patients with hematologic malignancies; generating protein spectra from the plasma samples with or without fractionation; comparing the protein spectra with clinical data; and identifying protein markers in the plasma samples that correlate with the clinical data. Protein markers identified by this approach can then be used to create a protein profile that can be used to diagnose the hematologic malignancy or determine the prognosis of the hematologic malignancy. Potentially these specific proteins can be identified and targeted in the therapy of these malignancies.

4 Claims, 19 Drawing Sheets

OTHER PUBLICATIONS

Kovarova et al., "Proteomics approach in classifying the biochemical basis of the anticancer activity of the new olomoucine-derived synthetic cyclin-dependent kinase inhibitor, bohemine," *Electrophoresis*, 21(17):3757-3764, 2000.

Niitsu et al., "Prognostic implications of the differentiation inhibitory factor nm23-H1 protein in the plasma of aggressive non-Hodgkin's lymphoma," *Blood*, 94(10):3541-3550, 1999.

Office Action, issued in U.S. Appl. No. 7,662,306, mailed Dec. 3, 2008.

Office Action, issued in U.S. Appl. No. 7,662,306, mailed Feb. 22, 2007.

Office Action, issued in U.S. Appl. No. 7,662,306, mailed Jun. 2, 2008.

Office Action, issued in U.S. Appl. No. 7,662,306, mailed Nov. 2, 2007.

Petricon et al., "Use of proteomic patterns in serum to identify ovarian cancer". *The Lancet*, 359:572-577, 2002.

Poley et al., "Evaluation of serum neural cell adhesion molecule as a prognostic marker in multiple myeloma," *Anticancer Res.*, 17:3021-3024, 1997.

Pusztai et al., "Pharmacoproteomic analysis of prechemotherapy and postchemotherapy plasma samples from patients receiving neoadjuvant or adjuvant chemotherapy for breast carcinoma," *Cancer*, 100: 1814-1822, 2004.

Verstovsek et al., "Plasma hepatocyte growth factor is a prognostic factor in patients with acute myeloid leukemia but not in patients with myelodysplastic syndrome," *Leukemia*, 15(8):1165-1170, 2001.

Verstovsek et al., "Significance of angiogenin plasma concentrations in patients with acute myeloid leukemia and advanced myelodysplastic syndrome," *Br. J. Haematol.*, 114(2):290-295, 2001.

Viniou et al., "Ida-FLAG plus imatinib mesylate-induced molecular remission in a patient with chemoresistant $Ph^1$ (+) acute myeloid leukemia," *Eur. J. Haematol.*, 72: 58-60, 2004, Abstract only.

Voss et al., "Correlation of clinical data with proteomics profiles in 24 patients with B-cell chronic lymphocyticleukemia," *Int. J. Cancer*, 91(2):180-186, 2001.

Wysocki et al., "Carcinoembryonic antigen, alphafetoprotein and alpha and beta subunits of human chorionic gonadotropin in plasma of children with acute leukemia," *Acta Paediatr. Hung.*, 28(2):119-125, 1987.

Yeoh et al., "Classification, subtype discovery, and prediction of outcome in pediatric acute lymphoblastic leukemia by gene expression profiling," *Cancer Cell*, 1(2):133-143, 2002.

Yokose and Ogata, "Plasma soluble interleukin-2 receptors in patients with myelodysplastic syndromes," *Leuk. Lymphoma*, 28:171-176, 1997.

Office Action issued in corresponding Japanese Patent Application No. 2007-509551, dated Mar. 10, 2011. (English Translation).

Office Action, issued in European Application No. 05 746 451.3-2404, mail date Oct. 20, 2009.

Office Communication in European Patent Application No. 05746451, dated Mar. 7, 2011.

Baggerly et at, "Reproducibility of SELD1-TOF protein patterns in serum: comparing datasests from different experiments," *Bioinformatics*, 20(5):777-785, 2004.

| Surface Fraction | Number of FP | M/Z |
|---|---|---|
| SAX2-Fraction2 | 5 | 12801.1732 |
| SAX2-Fraction2 | 6 | 13506.1515 |
| SAX2-Fraction2 | 6 | 518.8676 |
| SAX2-Fraction3 | 7 | 8127.5061 |
| IMAC3-Fraction1 | 5 | 5076.1814 |
| WCX2-Fraction2 | 5 | 41.8358 |
| SAX2-Fraction2 | 5 | 49877.3113 |
| WCX2-Fraction2 | 6 | 10127.7946 |
| IMAC3-Fraction1 | 6 | 3223.2382 |
| WCX2-Fraction2 | 8 | 8335.7003 |
| WCX2-Fraction2 | 9 | 5649.4968 |
| SAX2-Fraction2 | 7 | 8330.8957 |
| IMAC3-Fraction2 | 5 | 531.8963 |
| WCX2-Fraction2 | 6 | 9040.0205 |
| SAX2-Fraction2 | 6 | 12519.2897 |
| WCX2-Fraction2 | 6 | 65.0937 |
| SAX2-Fraction3 | 6 | 40019.1876 |
| WCX2-Fraction2 | 7 | 14616.859 |
| SAX2-Fraction2 | 9 | 86.7774 |
| WCX2-Fraction2 | 7 | 11677.6762 |
| WCX2-Fraction1 | 8 | 12241.7091 |
| WCX2-Fraction2 | 9 | 11411.8902 |
| WCX2-Fraction2 | 6 | 7361.645 |
| WCX2-Fraction1 | 6 | 11060.4231 |
| WCX2-Fraction2 | 9 | 37411.921 |
| SAX2-Fraction2 | 7 | 3067.3973 |
| SAX2-Fraction3 | 10 | 39008.5589 |
| SAX2-Fraction2 | 8 | 48423.466 |
| WCX2-Fraction3 | 9 | 5719.3364 |
| WCX2-Fraction2 | 5 | 10680.7025 |
| SAX2-Fraction2 | 5 | 8206.4623 |

*FIG. 5*

| Surface Fraction | Number of FP | M/Z |
|---|---|---|
| IMAC3-Fraction1 | 4 | 2533.253 |
| SAX2-Fraction2 | 3 | 12801.17 |
| SAX2-Fraction3 | 6 | 944.0915 |
| WCX2-Fraction2 | 4 | 11095.88 |
| IMAC3-Fraction1 | 6 | 2648.984 |
| SAX2-Fraction2 | 5 | 13506.15 |
| WCX2-Fraction2 | 5 | 12687.09 |
| SAX2-Fraction2 | 6 | 12519.29 |
| WCX2-Fraction4 | 4 | 207.8056 |
| SAX2-Fraction3 | 6 | 40019.19 |
| WCX2-Fraction2 | 4 | 12241.71 |
| WCX2-Fraction2 | 6 | 26397.83 |
| IMAC3-Fraction1 | 6 | 3223.238 |
| IMAC3-Fraction2 | 3 | 895.5696 |
| IMAC3-Fraction1 | 5 | 2675.053 |
| SAX2-Fraction2 | 6 | 518.8676 |
| SAX2-Fraction3 | 7 | 876.7685 |

*FIG. 6*

| Surface Fraction | Number of FP | M/Z |
|---|---|---|
| IMAC3-Fraction1 | 5 | 2533.2531 |
| IMAC3-Fraction2 | 3 | 895.5696 |
| SAX2-Fraction2 | 5 | 12801.173 |
| WCX2-Fraction3 | 7 | 11095.877 |
| SAX2-Fraction2 | 5 | 13506.152 |
| IMAC3-Fraction1 | 6 | 2648.9839 |
| SAX2-Fraction3 | 5 | 40019.188 |
| WCX2-Fraction2 | 6 | 26397.831 |
| WCX2-Fraction3 | 6 | 15269.208 |
| SAX2-Fraction2 | 6 | 12519.29 |
| SAX2-Fraction2 | 5 | 16424.507 |
| IMAC3-Fraction1 | 6 | 2509.4679 |
| SAX2-Fraction2 | 5 | 8330.8957 |
| SAX2-Fraction2 | 5 | 518.8676 |
| IMAC3-Fraction1 | 4 | 2274.7727 |
| SAX2-Fraction3 | 5 | 944.0915 |
| IMAC3-Fraction1 | 6 | 3223.2382 |
| WCX2-Fraction3 | 7 | 22130.579 |
| WCX2-Fraction4 | 4 | 207.8056 |
| IMAC3-Fraction4 | 6 | 9925.4222 |
| IMAC3-Fraction1 | 4 | 5076.1814 |
| SAX2-Fraction3 | 8 | 353.8245 |
| WCX2-Fraction2 | 6 | 14616.859 |
| SAX2-Fraction3 | 4 | 8127.5061 |
| WCX2-Fraction4 | 5 | 226.097 |
| IMAC3-Fraction1 | 5 | 2675.0528 |
| SAX2-Fraction3 | 5 | 6873.2851 |

*FIG. 7*

| Surface Fraction | Number of FP | M/Z |
|---|---|---|
| IMAC3-Fraction1 | 4 | 2533.253 |
| SAX2-Fraction2 | 3 | 12801.17 |
| WCX2-Fraction3 | 5 | 11095.88 |
| IMAC3-Fraction1 | 6 | 2648.984 |
| SAX2-Fraction3 | 6 | 944.0915 |
| SAX2-Fraction2 | 5 | 13506.15 |
| IMAC3-Fraction2 | 3 | 895.5696 |
| SAX2-Fraction2 | 6 | 12519.29 |
| SAX2-Fraction3 | 5 | 40019.19 |
| WCX2-Fraction2 | 6 | 26397.83 |
| WCX2-Fraction4 | 4 | 207.8056 |
| IMAC3-Fraction1 | 6 | 3223.238 |
| WCX2-Fraction2 | 5 | 12687.09 |
| SAX2-Fraction2 | 5 | 518.8676 |
| WCX2-Fraction3 | 6 | 15269.21 |
| SAX2-Fraction2 | 6 | 16424.51 |
| SAX2-Fraction2 | 6 | 8330.896 |
| IMAC3-Fraction1 | 5 | 2675.053 |
| IMAC3-Fraction1 | 6 | 2509.468 |
| WCX2-Fraction2 | 4 | 12241.71 |
| IMAC3-Fraction4 | 6 | 9925.422 |
| WCX2-Fraction3 | 7 | 22130.58 |

*FIG. 8*

USING PLASMA PROTEOMIC PATTERN FOR DIAGNOSIS, CLASSIFICATION, PREDICTION OF RESPONSE TO THERAPY AND CLINICAL BEHAVIOR, STRATIFICATION OF THERAPY, AND MONITORING DISEASE IN HEMATOLOGIC MALIGNANCIES

This application is a divisional of U.S. application Ser. No. 11/110,374, filed Apr. 20, 2005, now issued as U.S. Pat. No. 7,622,306, which claims priority to U.S. Provisional Patent Application Ser. No. 60/563,873, filed Apr. 20, 2004. The above-referenced applications are incorporated herein by reference in their entirety.

BACKGROUND OF THE INVENTION

1. Field of the Invention

The present invention relates generally to the fields of proteomics. More particularly, it concerns the use of proteomics for diagnosis and the prognosis of hematologic malignancies. Also, the invention relates to predicting the response to therapy and stratifying patients for therapy.

2. Description of Related Art

Hematologic malignancies are cancers of the blood and bone marrow, including leukemia and lymphoma. Leukemia is a malignant neoplasm characterized by abnormal proliferation of leukocytes and is one of the four major types of cancer. Leukemia is diagnosed in about 29,000 adults and 2,000 children each year in the United States. Leukemias are classified according to the type of leukocyte most prominently involved. Acute leukemias are predominantly undifferentiated cell populations and chronic leukemias have more mature cell forms.

The acute leukemias are divided into lymphoblastic (ALL) and non-lymphoblastic (ANLL) types and may be further subdivided by morphologic and cytochemical appearance according to the French-American-British classification or according to their type and degree of differentiation. Specific B- and T-cell, as well as myeloid cell surface markers/antigens are used in the classification too. ALL is predominantly a childhood disease while ANLL, also known as acute myeloid leukemia (AML), is a more common acute leukemia among adults.

Chronic leukemias are divided into lymphocytic (CLL) and myeloid (CML) types. CLL is characterized by the increased number of mature lymphocytes in blood, bone marrow, and lymphoid organs. Most CLL patients have clonal expansion of lymphocytes with B cell characteristics. CLL is a disease of older persons. In CML, the granulocytic cells predominate at all stages of differentiation in blood and bone marrow, but may also affect liver, spleen, and other organs.

Among patients with leukemia there can be a highly variable clinical course as reflected by varying survival times and resistance to therapy. Reliable individual prognostic tools are limited at present. Advances in proteomic technologies may provide new diagnostic and prognostic indicators for hematologic malignancies such as leukemia.

The term "proteome" refers to all the proteins expressed by a genome, and thus proteomics involves the identification of proteins in the body and the determination of their role in physiological and pathophysiological functions. The ~30,000 genes defined by the Human Genome Project translate into 300,000 to 1 million proteins when alternate splicing and post-translational modifications are considered. While a genome remains unchanged to a large extent, the proteins in any particular cell change dramatically as genes are turned on and off in response to their environment.

As a reflection of the dynamic nature of the proteome, some researchers prefer to use the term "functional proteome" to describe all the proteins produced by a specific cell in a single time frame. Ultimately, it is believed that through proteomics, new disease markers and drug targets can be identified.

Proteomics has previously been used in the study of leukemia. For example, two-dimensional polyacrylamide gel electrophoresis (2-D PAGE) of proteins from the lymphoblasts of patients with ALL was used to identify polypeptides that could distinguish between the major subgroups of ALL (Hanash et al., 1986). In other studies of ALL using 2-D PAGE, distinct levels of a polypeptide were observed between infants and older children with otherwise similar cell surface markers (Hanash et al., 1989). Voss et al. demonstrated that B-CLL patient populations with shorter survival times exhibited changed levels of redox enzymes, Hsp27, and protein disulfide isomerase, as determined by 2-D PAGE of proteins prepared from mononuclear cells (Voss et al., 2001).

As these studies indicate, proteomics can be a useful tool in the study of hematologic malignancies. There is, however, a need for proteomics techniques that are more reliable and simple than those currently available in the art.

SUMMARY OF THE INVENTION

The present invention provides a novel approach that uses plasma proteomics to create a profile that can be used to diagnose hematologic malignancies and predict a patient's clinical behavior and response to therapy.

In one embodiment, the invention provides a method of creating a diagnostic or prognostic protein profile of a hematologic malignancy comprising: obtaining plasma samples from a population of patients with hematologic malignancies; generating protein spectra from the plasma samples; comparing the protein spectra with patients' clinical data relating to the hematologic malignancy; identifying a protein marker or group of protein markers in the plasma samples that correlate with the clinical data; and creating a protein profile based on the identified protein marker or group of protein markers, wherein the protein profile can be used to diagnose the hematologic malignancy or determine the prognosis of the hematologic malignancy.

In a preferred embodiment, the protein spectra is generated by mass spectrometry. The mass spectrometry may be, for example, SELDI (surface enhanced laser desorption/ionization), MALDI (matrix assisted desorption/ionization), or Tandem mass spectrometry (MS/MS). In other embodiments of the invention, the protein spectra is generated by two-dimensional gel electrophoresis. In certain aspects, the protein samples are fractionated before mass spectrometry analysis or two-dimensional gel electrophoresis. Fractionation can be according to a variety of properties, such as pH, size, structure, or binding affinity. In one aspect, plasma proteins are fractionated into 4 different fractions according to pH using strong anion exchange column (Fraction1=pH9, pH7, Fraction2=pH5, Fraction3=pH4, Fraction4=pH3, organic).

In certain aspects, the protein marker or group of protein markers that correlate with the clinical data are identified by univariate statistics, multivariate statistics, or hierarchical cluster analysis. In a preferred embodiment, the protein marker or group of protein markers that correlate with the clinical data are identified using correlation statistics with beta-uniform mixture analysis, genetic algorithms, univariate, and/or multivariate statistics. In other preferred embodiment, the protein marker or group of protein markers that correlate with the clinical data are identified using a decision tree algorithm. In some embodiments of the invention the clinical data comprises one or more of cytogenetics, age, performance status, response to therapy, type of therapy, progression, event-free survival, time from response to relapse, and survival time.

In preferred embodiments, the protein profile is used to diagnose the hematologic malignancy; classify the type of hematologic malignancy; predict a patient's response to drug therapy; predict a patient's survival time; or predict a patient's time from response to relapse. In certain embodiments, the hematologic malignancy is leukemia, non-Hodgkin lymphoma, Hodgkin lymphoma, myeloma, or myelodysplastic syndrome. The leukemia may be acute myeloid leukemia (AML), chronic myeloid leukemia (CML), acute lymphocytic leukemia (ALL), or chronic lymphocytic leukemia (CLL).

In another embodiment, the invention provides a method of predicting response to therapy in a patient with a hematologic malignancy comprising: obtaining a plasma sample from a patient; identifying a protein marker or group of protein markers in the plasma sample that is associated with response to therapy; and predicting the patient's response to therapy. In a preferred embodiment the hematologic malignancy is leukemia, non-Hodgkin lymphoma, Hodgkin lymphoma, myeloma, or myelodysplastic syndrome. The leukemia may be acute myeloid leukemia (AML), chronic myeloid leukemia (CML), acute lymphocytic leukemia (ALL), or chronic lymphocytic leukemia (CLL).

The method may be used to predict a patient's response to therapy before beginning therapy, during therapy, or after therapy is completed. For example, by predicting a patient's response to therapy before beginning therapy, the information may be used in determining the best therapy option for the patient.

In one aspect of the invention, the protein marker is a peak. The peak may be generated by mass spectrometry. The mass spectrometry may be, for example, SELDI, MALDI, or MS/MS. In another aspect of the invention, the protein marker is a spot. In a preferred embodiment the spot is generated by two-dimensional gel electrophoresis.

In certain embodiments of the invention the therapy is chemotherapy, immunotherapy, antibody-based therapy, radiation therapy, or supportive therapy (essentially any implemented for leukemia). In some embodiments, the chemotherapy is Gleevac or idarubicin and ara-C.

In some embodiments the protein marker or group of protein markers associated with response to a specific therapy in a patient with AML is one or more of Peak 1 to Peak 17 generated by SELDI mass spectrometry as defined in Table 1 below. In one embodiment, the group of protein markers associated with response to a specific therapy in a patient with AML comprises Peak 1 and Peak 2.

TABLE 1

Protein peaks generated by SELDI-TOF MS that are associated with response to therapy in patients with AML.

| Peak | Surface/Fraction | Approximate Molecular Weight (Daltons) |
|---|---|---|
| Peak 1 | IMAC3-Fraction1 | 2533.253 |
| Peak 2 | SAX2-Fraction2 | 12801.17 |
| Peak 3 | SAX2-Fraction3 | 944.0915 |

TABLE 1-continued

Protein peaks generated by SELDI-TOF MS that are associated with response to therapy in patients with AML.

| Peak | Surface/Fraction | Approximate Molecular Weight (Daltons) |
|---|---|---|
| Peak 4 | WCX2-Fraction3 | 11095.88 |
| Peak 5 | IMAC3-Fraction1 | 2648.984 |
| Peak 6 | SAX2-Fraction2 | 13506.15 |
| Peak 7 | WCX2-Fraction2 | 12687.09 |
| Peak 8 | SAX2-Fraction2 | 12519.29 |
| Peak 9 | WCX2-Fraction4 | 207.8056 |
| Peak 10 | SAX2-Fraction3 | 40019.19 |
| Peak 11 | WCX2-Fraction2 | 12241.71 |
| Peak 12 | WCX2-Fraction2 | 26397.83 |
| Peak 13 | IMAC3-Fraction1 | 3223.238 |
| Peak 14 | IMAC3-Fraction2 | 895.5696 |
| Peak 15 | IMAC3-Fraction1 | 2675.053 |
| Peak 16 | SAX2-Fraction2 | 518.8676 |
| Peak 17 | SAX2-Fraction3 | 876.7685 |

Surface/Fraction indicates the surface (anion exchange (SAX), cation exchange (WCX), or metal affinity chip (IMAC)) and the fraction (Fraction1 ≡ pH9, pH7, Fraction2 ≡ pH5, Fraction3 ≡ pH4, Fraction4 ≡ pH3, organic) from which the protein spectra was generated.

In one embodiment, the invention provides a method of predicting time to relapse in a patient with a hematologic malignancy comprising: obtaining a plasma sample from a patient; identifying a protein marker or group of protein markers in the plasma sample that is associated with time to relapse; and predicting the patient's time to relapse. In a preferred embodiment the hematologic malignancy is leukemia, non-Hodgkin lymphoma, Hodgkin lymphoma, myeloma, or myelodysplastic syndrome. The leukemia may be acute myeloid leukemia (AML), chronic myeloid leukemia (CML), acute lymphocytic leukemia (ALL), or chronic lymphocytic leukemia (CLL).

In one aspect of the invention, the protein marker is a peak. The peak may be generated by mass spectrometry. Preferably the peak is generated by SELDI mass spectrometry. In another aspect of the invention, the protein marker is a spot. In a preferred embodiment the spot is generated by two-dimensional gel electrophoresis.

In a preferred embodiment the protein marker or group of protein markers associated with time from response to idarubicin and ara-C to relapse in a patient with AML is one or more of the Peak 18 to Peak 29 generated by SELDI mass spectrometry as defined in Table 2 below.

TABLE 2

Protein peaks generated by SELDI-TOF MS that are associated with time from response to therapy to relapse in patients with AML.

| Peak | Surface-Fraction | Approximate Molecular Weight (Daltons) |
|---|---|---|
| Peak 18 | IMAC3-Fraction3 | 12139.4335 |
| Peak 19 | WCX2-Fraction2 | 11677.6762 |
| Peak 20 | IMAC3-Fraction3 | 11483.9713 |
| Peak 21 | IMAC3-Fraction3 | 11322.1079 |
| Peak 22 | SAX2-Fraction2 | 11095.8768 |
| Peak 23 | WCX2-Fraction1 | 7831.326 |
| Peak 24 | IMAC3-Fraction4 | 11481.7153 |
| Peak 25 | IMAC3-Fraction3 | 12235.8865 |
| Peak 26 | WCX2-Fraction4 | 797.602 |
| Peak 27 | WCX2-Fraction4 | 783.9856 |

TABLE 2-continued

Protein peaks generated by SELDI-TOF MS that are associated with time from response to therapy to relapse in patients with AML.

| Peak | Surface-Fraction | Approximate Molecular Weight (Daltons) |
|---|---|---|
| Peak 28 | WCX2-Fraction2 | 11884.4738 |
| Peak 29 | WCX2-Fraction4 | 2507.8862 |

Surface/Fraction indicates the surface (anion exchange (SAX), cation exchange (WCX), or metal affinity chip (IMAC)) and the fraction (Fraction1 = pH9, pH7, Fraction2 = pH5, Fraction3 = pH4, Fraction4 = pH3, organic) from which the protein spectra was generated.

In a preferred embodiment the protein marker or group of protein markers associated with relapse in a patient with ALL is one or more of the Peak 30 to Peak 49 generated by SELDI mass spectrometry as defined in Table 3 below.

TABLE 3

Protein Peaks generated by SELDI-TOF MS that are the strongest predictors for relapse in patients with ALL.

| Peak | Fraction type | Approximate Molecular Weight (Daltons) |
|---|---|---|
| Peak 30 | WCX2/pH9 | 7727.972 |
| Peak 31 | IMAC3/pH4 | 61940.76 |
| Peak 32 | SAX2/pH3 | 124797.7 |
| Peak 33 | WCX2/pH9 | 53623.64 |
| Peak 34 | WCX2/pH9 | 10216.72 |
| Peak 35 | SAX2/pH4 | 145023.4 |
| Peak 36 | SAX2/pH5 | 6808.864 |
| Peak 37 | WCX2/pH9 | 7249.661 |
| Peak 38 | WCX2/pH9 | 6588.005 |
| Peak 39 | WCX2/pH9 | 78971.03 |
| Peak 40 | WCX2/pH9 | 4924.562 |
| Peak 41 | IMAC3/pH4 | 55864.83 |
| Peak 42 | WCX2/pH9 | 6801.569 |
| Peak 43 | WCX2/pH9 | 13298.19 |
| Peak 44 | SAX2/pH3 | 83531.42 |
| Peak 45 | WCX2/pH9 | 39542.43 |
| Peak 46 | WCX2/pH9 | 159276.8 |
| Peak 47 | SAX2/pH4 | 106256.1 |
| Peak 48 | WCX2/pH9 | 88687.58 |
| Peak 49 | IMAC3/pH9 | 135305.2 |

In a preferred embodiment the protein marker or group of protein markers that differentiate between patients with L1/L2 ALL and patients with L3 ALL is one or more of the Peak 50 to Peak 69 generated by SELDI mass spectrometry as defined in Table 4 below.

TABLE 4

Protein Peaks generated by SELDI-TOF MS that are the strongest differentiators between L1/L2 ALL and L3 ALL.

| Peak | Fraction Type | Approximate Molecular Weight (Daltons) |
|---|---|---|
| Peak 50 | WCX2/pH9 | 7727.865343 |
| Peak 51 | WCX2/pH9 | 10214.09619 |
| Peak 52 | IMAC3/pH5 | 9263.336516 |
| Peak 53 | IMAC3/pH9 | 10217.12293 |
| Peak 54 | IMAC3/pH9 | 7722.657526 |
| Peak 55 | WCX2/pH5 | 7728.041349 |
| Peak 56 | WCX2/pH9 | 9268.979905 |
| Peak 57 | IMAC3/pH5 | 7741.020002 |
| Peak 58 | WCX2/pH3 | 9248.709422 |
| Peak 59 | WCX2/pH3 | 7720.190664 |
| Peak 60 | SAX2/pH3 | 13870.3916 |
| Peak 61 | IMAC3/pH4 | 7725.474001 |
| Peak 62 | IMAC3/pH9 | 9275.311795 |
| Peak 63 | SAX2/pH4 | 41782.2775 |
| Peak 64 | WCX2/pH9 | 8896.712054 |
| Peak 65 | WCX2/pH3 | 4911.78345 |
| Peak 66 | SAX2/pH4 | 83363.03733 |
| Peak 67 | SAX2/pH4 | 45087.95748 |
| Peak 68 | SAX2/pH4 | 121673.475 |
| Peak 69 | IMAC3/pH3 | 7727.155842 |

Those skilled in the art will recognize that the specific identity of the proteins represented by the protein markers described herein, or of protein markers revealed by the methods described herein, is not necessary to create or utilize a diagnostic or prognostic protein profile. The presence or absence, or increased or decreased levels, of a protein marker or group of protein markers can be used to create or utilize a diagnostic or prognostic protein profile without knowledge of what the proteins are. For example, a diagnostic or prognostic protein profile could be created or utilized based on the pattern of a group of protein markers without needing to know the specific identity of the protein markers in the pattern.

In another embodiment, the invention provides a method of predicting response to therapy in a patient with a hematologic malignancy comprising: obtaining a bone marrow aspirate sample from a patient; identifying a protein marker or group of protein markers in the sample that is associated with response to therapy; and predicting the patient's response to therapy. In a preferred embodiment the hematologic malignancy is leukemia, non-Hodgkin lymphoma, Hodgkin lymphoma, myeloma, or myelodysplastic syndrome. The leukemia may be acute myeloid leukemia (AML), chronic myeloid leukemia (CML), acute lymphocytic leukemia (ALL), or chronic lymphocytic leukemia (CLL). In one aspect of the invention, the leukemia is CML.

In certain aspects, a protein marker of the present invention may be a P52rIPK homolog, follistatin-related protein 1 precursor, annexin A10, annexin 14, tumor necrosis factor receptor superfamily member XEDAR, a zinc finger protein, CD38 ADP-ribosyl cyclase 1, connective tissue growth factor, CD28, Bcl2-related ovarian killer, tumor necrosis factor receptor superfamily member 10D, X-linked ectodysplasin receptor, ectodysplain A2 isoform receptor, or chromosome 21 open reading frame 63.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A shows a histogram of the p-values for predicting response to therapy using multivariate logistic model incorporating all the above variables. Each P value represents the effects of adding one peak. As shown in the histogram, at low P values, the transformation is not uniform, which indicates that these values represent specific predictions.

FIG. 1B shows that the false positivity (predicting response) increases significantly with P-values >0.005.

In FIG. 1C the relation between posterior probability and p-value is shown. This demonstrates that the P-value should be <0.01 to have adequate posterior predictive value.

FIG. 1D shows the receiver operating characteristics (ROC) curve as the cutoff for single-test p-values changes. Sensitivity is shown on the Y-axis and specificity is shown on the X-axis.

FIG. 2A shows a histogram of the p-values for predicting response to therapy using multivariate logistic model incorporating all the above variables. Each P value represents the effects of adding one peak. As shown in the histogram, at low P values, the transformation is not uniform, which indicates that these values represent specific predictions.

FIG. 2B shows that the false positivity (predicting response) increases significantly with P-values >0.005.

In FIG. 2C the relation between posterior probability and p-value is shown. This demonstrates that the P-value should be <0.01 to have adequate posterior predictive value.

FIG. 2D shows the receiver operating characteristics (ROC) curve as the cutoff for single-test p-values changes. Sensitivity is shown on the Y-axis and specificity is shown on the X-axis.

FIG. 3A shows a histogram of the p-values for predicting response to therapy using multivariate logistic model incorporating all the above variables. Each P value represents the effects of adding one peak. As shown in the histogram, at low P values, the transformation is not uniform, which indicates that these values represent specific predictions.

FIG. 3B shows that the false positivity (predicting response) increases significantly with P-values >0.01.

In FIG. 3C the relation between posterior probability and p-value is shown. This demonstrates that the P-value should be <0.01 to have adequate posterior predictive value.

FIG. 4A-D: Analysis of the p-values as a beta-uniform mixture where the transformed peak value (logPeak+Peak) was added to the base model (Response~Cytogenetics+Performance.Status+Age) to predict response to therapy in patients with AML. FIG. 4A shows a histogram of the p-values for predicting response to therapy using multivariate logistic model incorporating all the above variables. Each P value represents the effects of adding one peak. As shown in the histogram, at low P values, the transformation is not uniform, which indicates that these values represent specific predictions.

FIG. 4B shows that the false positivity (predicting response) increases significantly with P-values >0.01.

In FIG. 4C the relation between posterior probability and p-value is shown. This demonstrates that the P-value should be <0.01 to have adequate posterior predictive value.

FIG. 5: Significant peaks for (logPeak) transformed data for predicting response to therapy in patients with AML. The False Discovery Rate was set at 0.2. The first column shows the Fraction (Fraction1=pH9,pH7, Fraction2=pH5, Fraction3=pH4, or Fraction4=pH3, organic) and Surface (anion exchange (SAX), cation exchange (WCX), or metal affinity chip (IMAC)) analyzed by SELDI mass spectrometry. The second column shows the number of False Positives when the transformed peak value was added to the base model (Response~Cytogenetics+Performance.Status+Age) to predict response to therapy in patients with AML. The third column shows the mass-to-charge ratio (M/Z) of the peak.

FIG. 6: Significant peaks for (logPeak+(logPeak)$^2$) transformed data for predicting response to therapy in patients with AML. The False Discovery Rate was set at 0.1. The first column shows the Fraction (Fraction1=pH9,pH7, Fraction2=pH5, Fraction3=pH4, or Fraction4=pH3, organic) and Surface (anion exchange (SAX), cation exchange (WCX), or metal affinity chip (IMAC)) analyzed by SELDI mass spectrometry. The second column shows the number of False Positives when the transformed peak value was added to the base model (Response~Cytogenetics+Performance.Status+Age) to predict response to therapy in patients with AML. The third column shows the mass-to-charge ratio (M/Z) of the peak.

FIG. 7: Significant peaks for (Peak+Peak$^2$) transformed data for predicting response to therapy in patients with AML. The False Discovery Rate was set at 0.1. The first column shows the Fraction (Fraction1=pH9,pH7, Fraction3=pH4, or Fraction4=pH3, organic) and Surface (anion exchange (SAX), cation exchange (WCX), or metal affinity chip (IMAC)) analyzed by SELDI mass spectrometry. The second column shows the number of False Positives when the transformed peak value was added to the base model (Response~Cytogenetics+Performance.Status+Age) to predict response to therapy in patients with AML. The third column shows the mass-to-charge ratio (M/Z) of the peak.

FIG. 8: Significant peaks for (Peak+logPeak) transformed data for predicting response to therapy in patients with AML. The False Discovery Rate was set at 0.1. The first column shows the Fraction (Fraction1=pH9,pH7, Fraction2=pH5, Fraction3=pH4, or Fraction4=pH3, organic) and Surface (anion exchange (SAX), cation exchange (WCX), or metal affinity chip (IMAC)) analyzed by SELDI mass spectrometry. The second column shows the number of False Positives when the transformed peak value was added to the base model (Response~Cytogenetics+Performance.Status+Age) to predict response to therapy in patients with AML. The third column shows the mass-to-charge ratio (M/Z) of the peak.

FIG. 9A shows a histogram of the p-values for predicting response to therapy using multivariate logistic model incorporating all the above variables. Each P value represents the effects of adding one peak. As shown in the histogram, at low P values, the transformation is not uniform, which indicates that these values represent specific predictions.

FIG. 9B shows that the false positivity (predicting response) increases significantly with P-value.

In FIG. 9C the relation between posterior probability and p-value is shown. This demonstrates that the P-value should be <0.01 to have adequate posterior predictive value.

FIG. 9D shows the receiver operating characteristics (ROC) curve as the cutoff for single-test p-values changes. Sensitivity is shown on the Y-axis and specificity is shown on the X-axis.

FIG. 10A shows a histogram of the p-values for predicting response to therapy using multivariate logistic model incorporating all the above variables. Each P value represents the effects of adding one peak. FIG. 10B shows the false positivity (predicting response). In FIG. 10C the relation between posterior probability and p-value is shown. FIG. 10D shows the receiver operating characteristics (ROC) curve, with sensitivity shown on the Y-axis and specificity shown on the X-axis. It is evident from FIGS. 10A-D that there are no significant peaks.

DESCRIPTION OF ILLUSTRATIVE EMBODIMENTS

A. The Present Invention

Figure 1A:
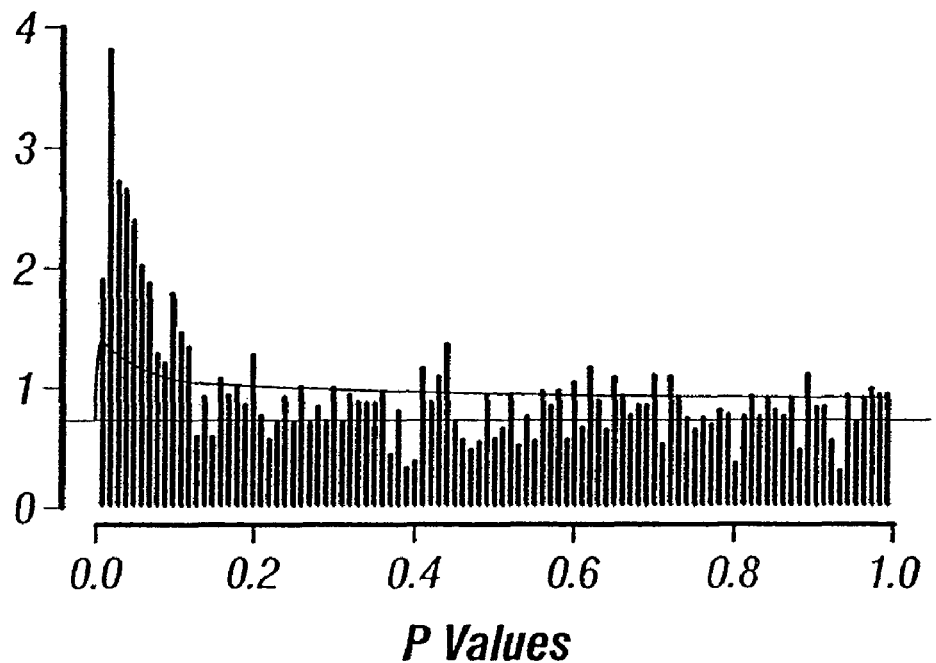
FIG. 1A-D: Analysis of the p-values as a beta-uniform mixture where the transformed peak value (logPeak) was added to the base model (Response~Cytogenetics+Performance.Status+Age) to predict response to therapy in patients with AML.
Figure 1B:
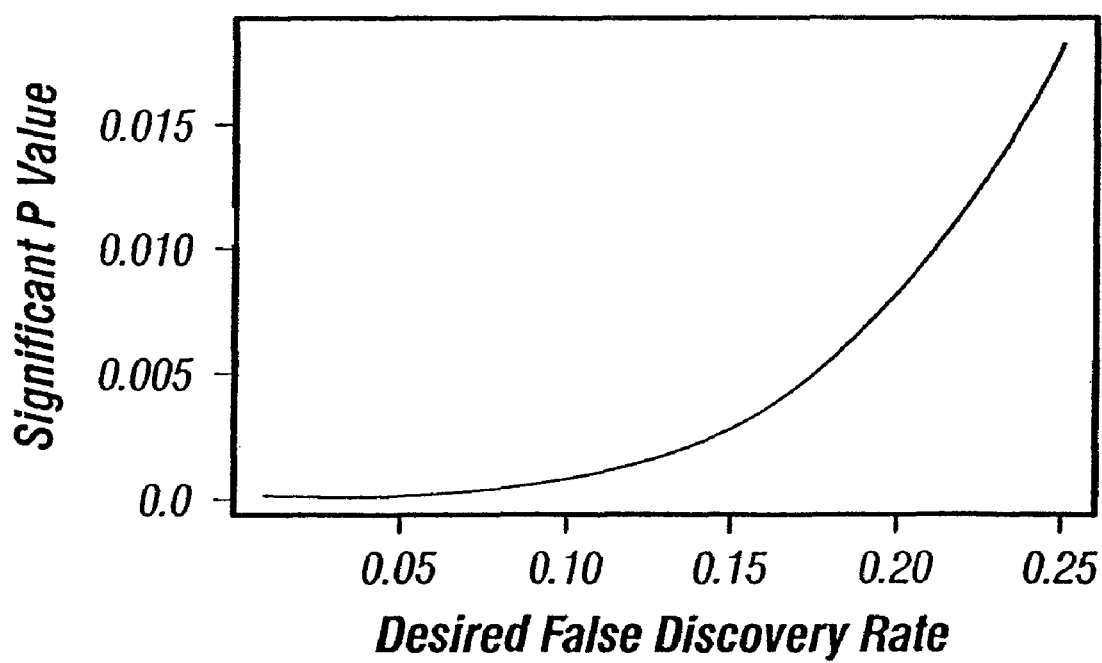
Figure 1C:
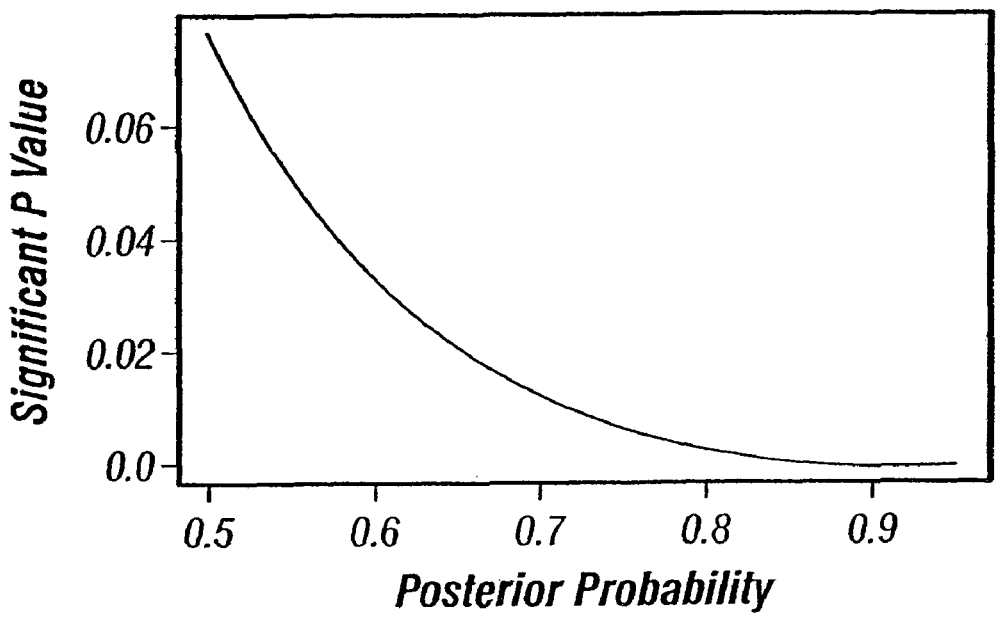
Figure 1D:
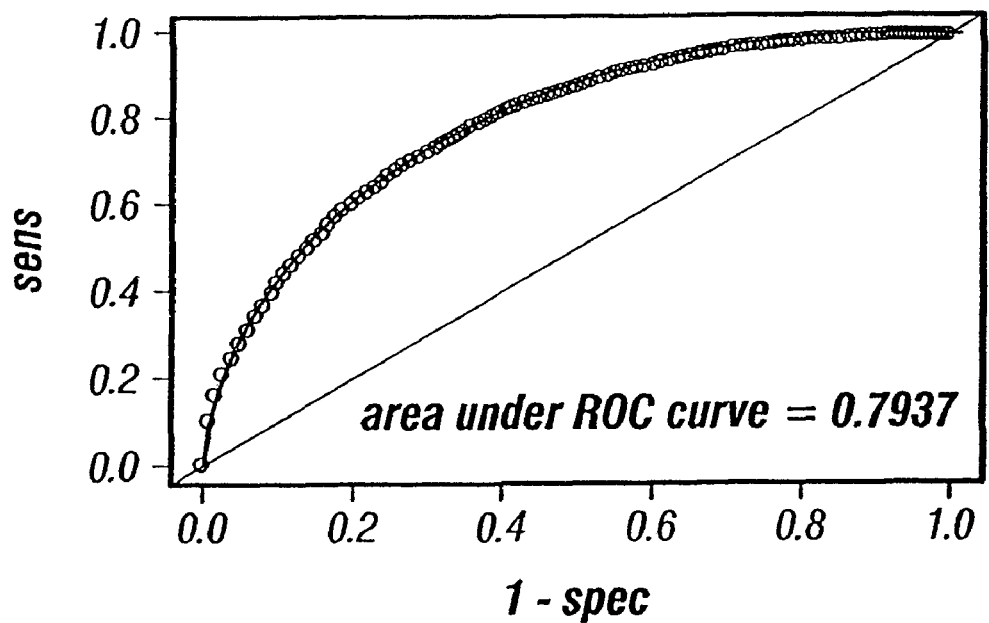
Figure 2A:
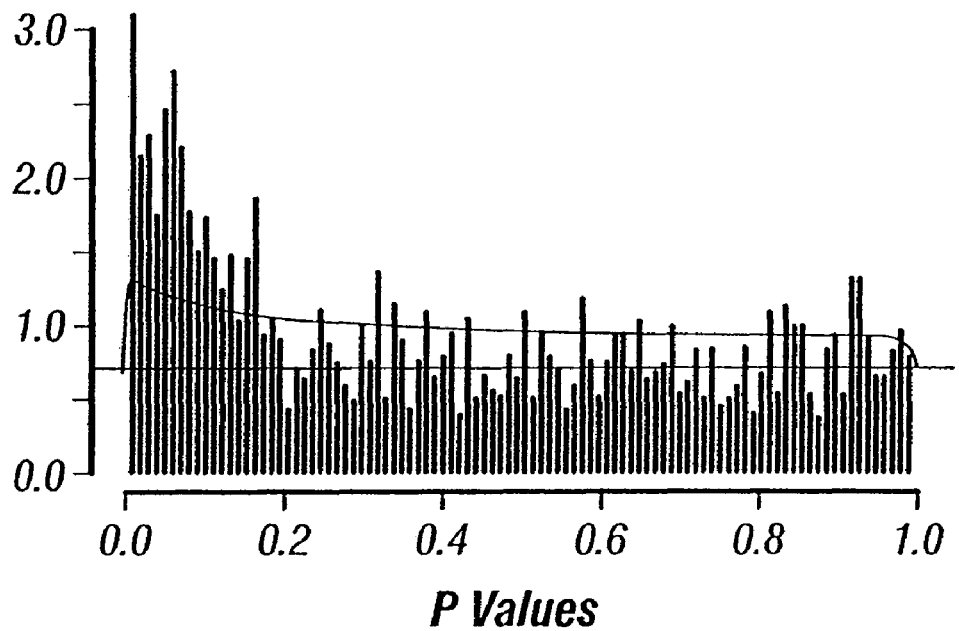
FIG. 2A-D: Analysis of the p-values as a beta-uniform mixture where the transformed peak value (logPeak+(logPeak)$^2$) was added to the base model (Response~Cytogenetics+Performance.Status+Age) to predict response to therapy in patients with AML.
Figure 2B:
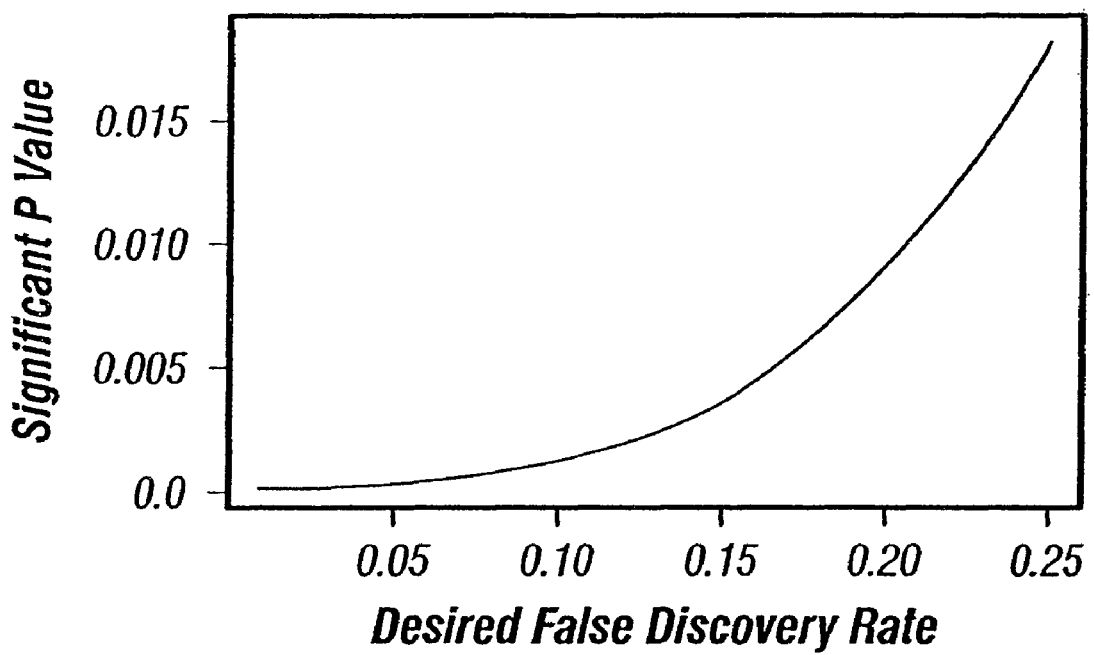
Figure 2C:
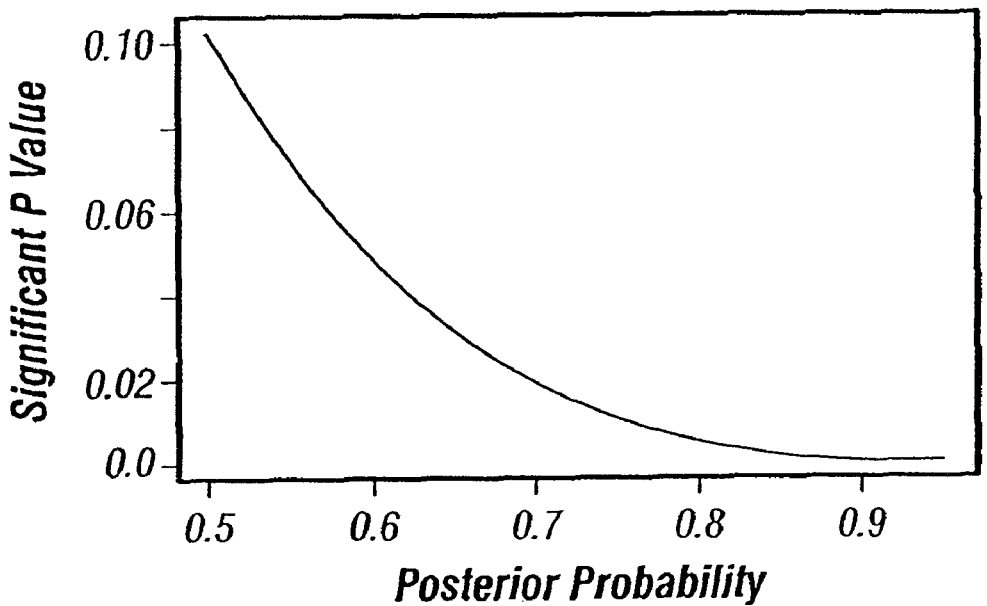
Figure 2D:
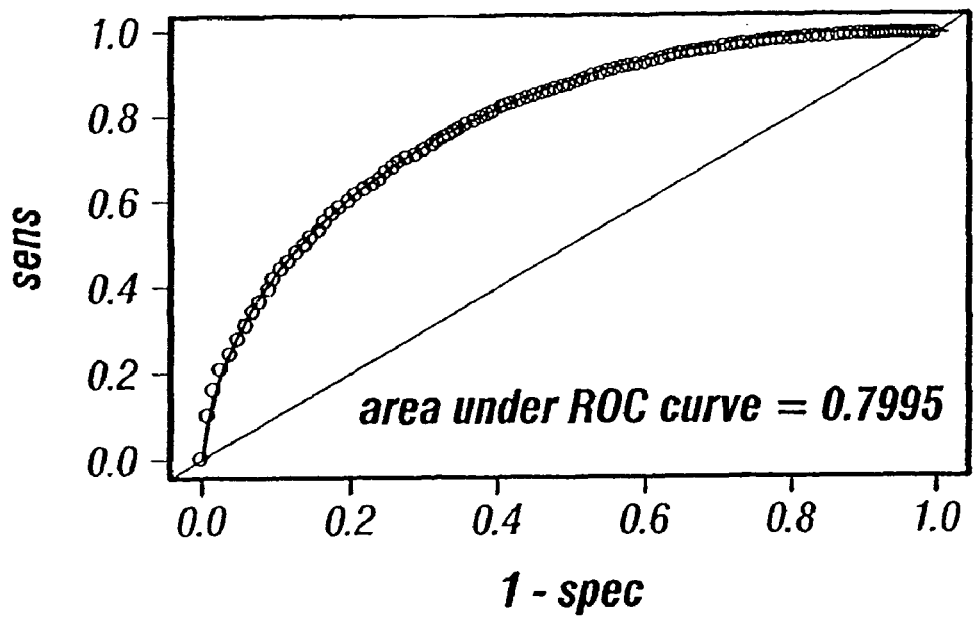
Figure 3A:
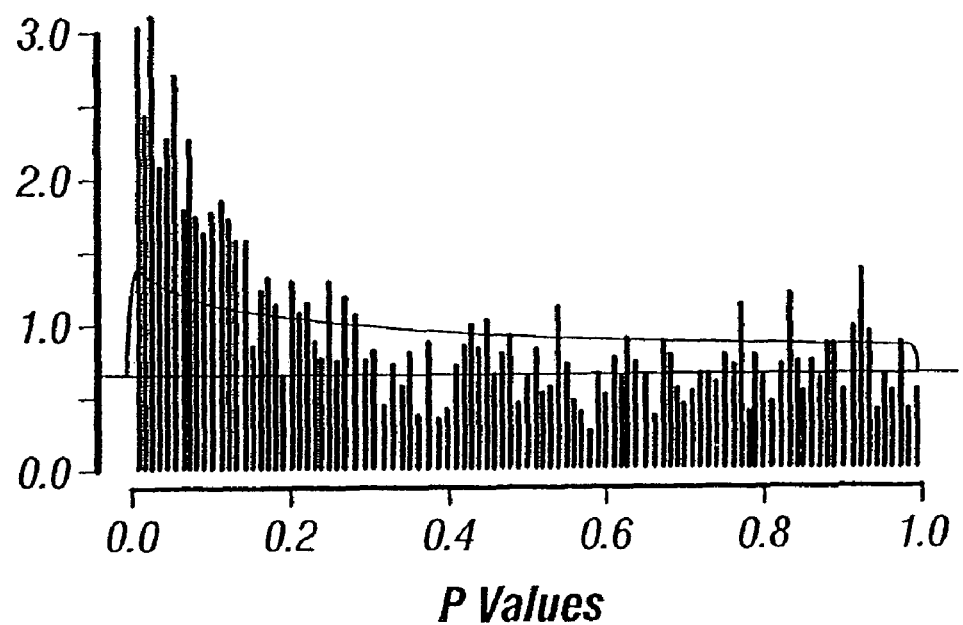
FIG. 3A-D: Analysis of the p-values as a beta-uniform mixture where the transformed peak value (Peak+Peak$^2$) was added to the base model (Response~Cytogenetics+Performance.Status+Age) to predict response to therapy in patients with AML.
Figure 3B:
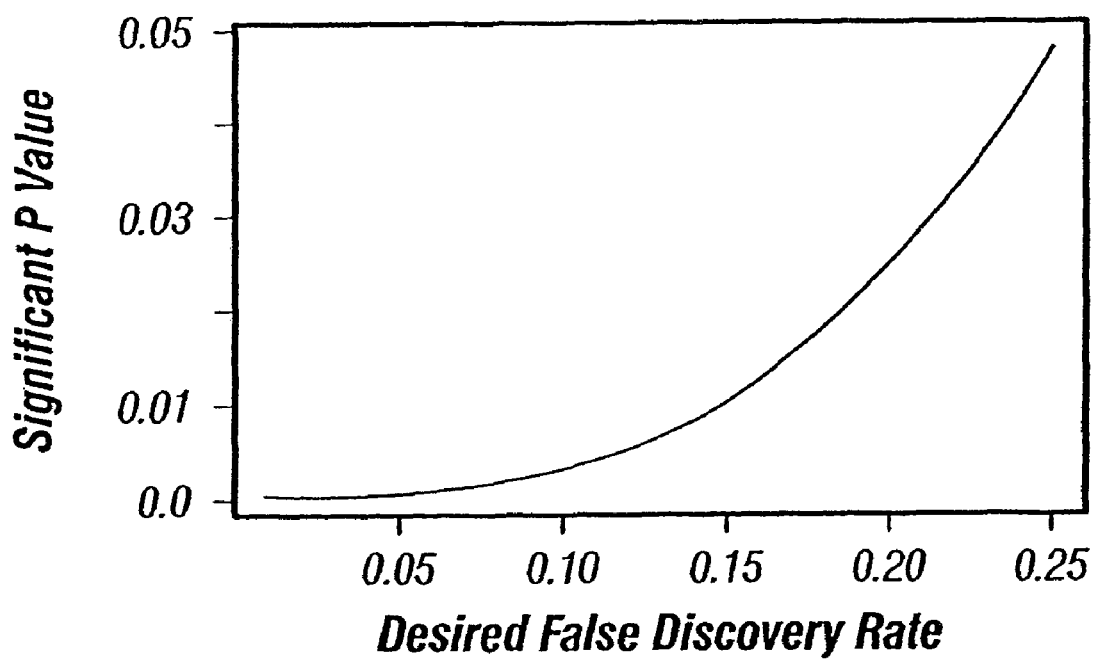
Figure 3C:
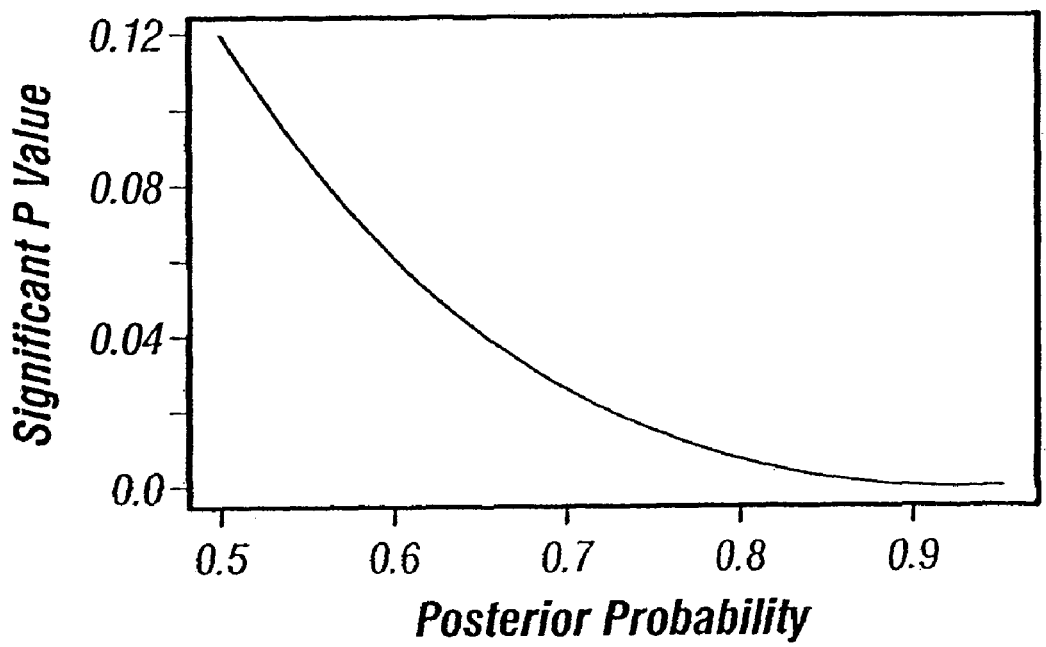
Figure 3D:
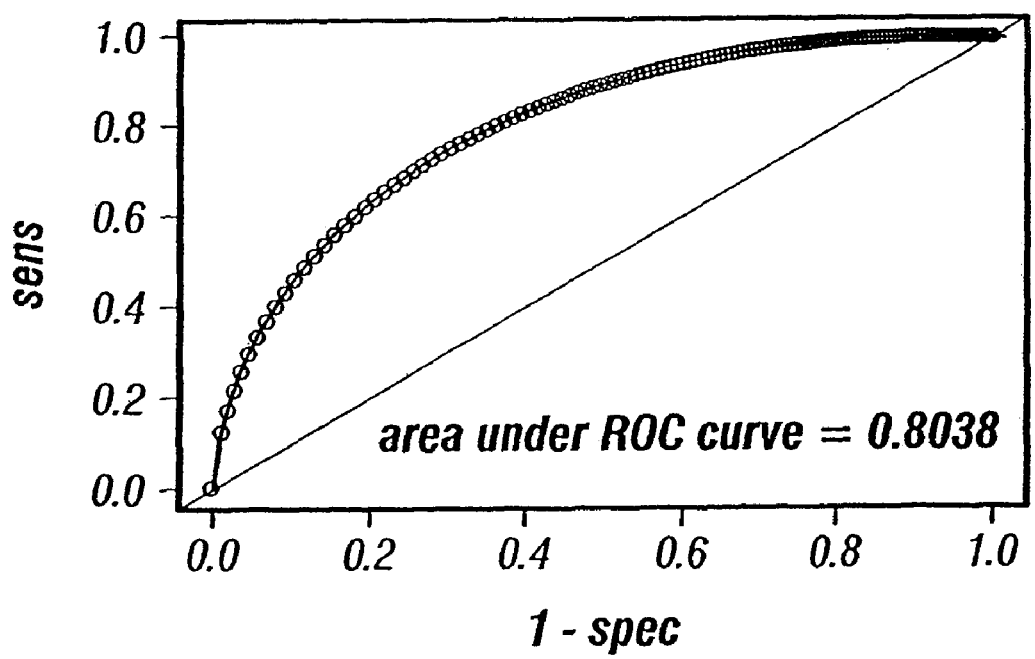
Figure 4A:
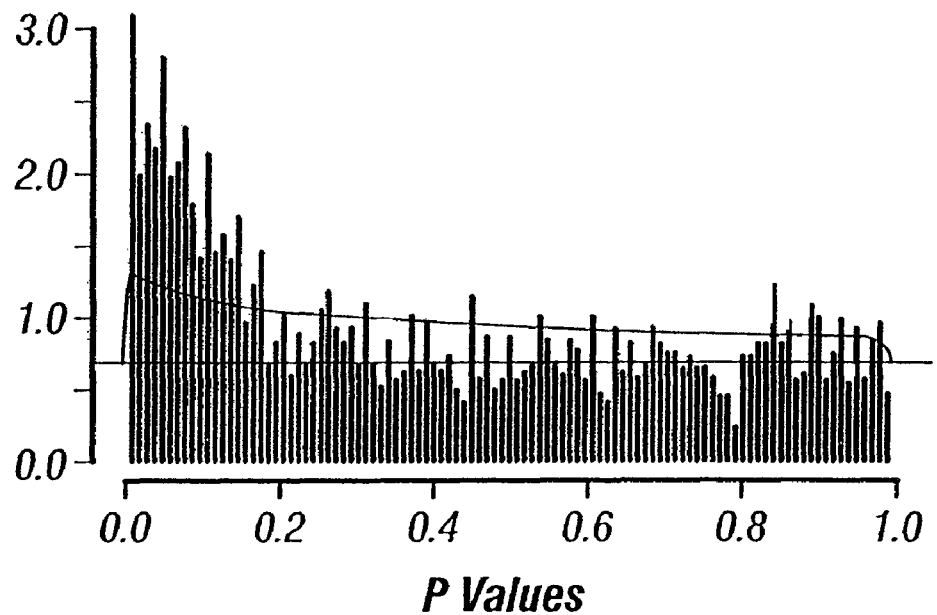
Figure 4B:
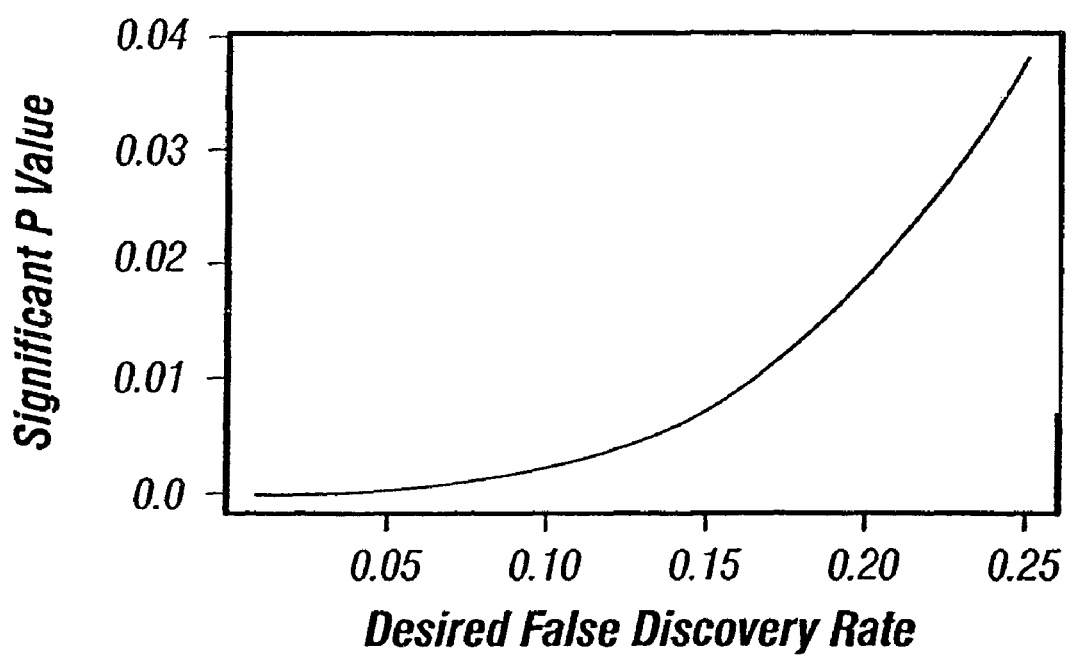
Figure 4C:
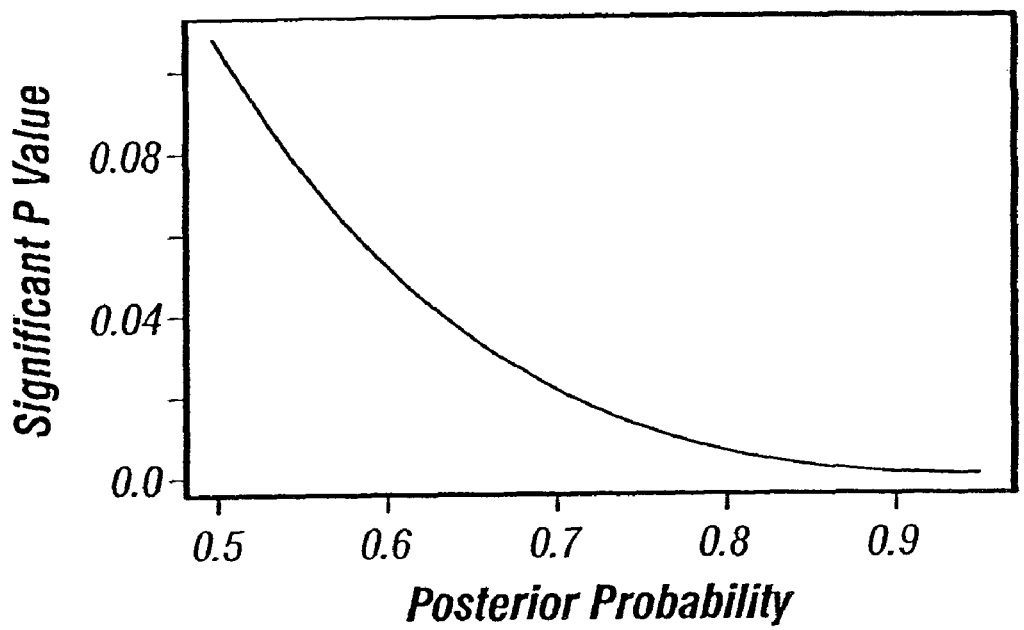
Figure 4D:
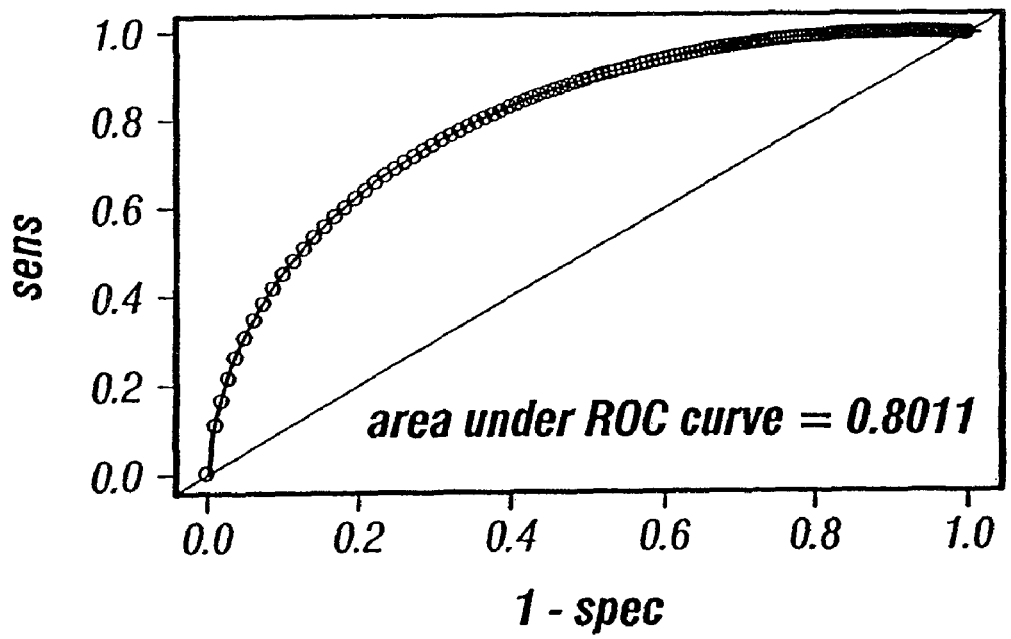
FIG. 4D shows the receiver operating characteristics (ROC) curve as the cutoff for single-test p-values changes. Sensitivity is shown on the Y-axis and specificity is shown on the X-axis.
Figure 9A:
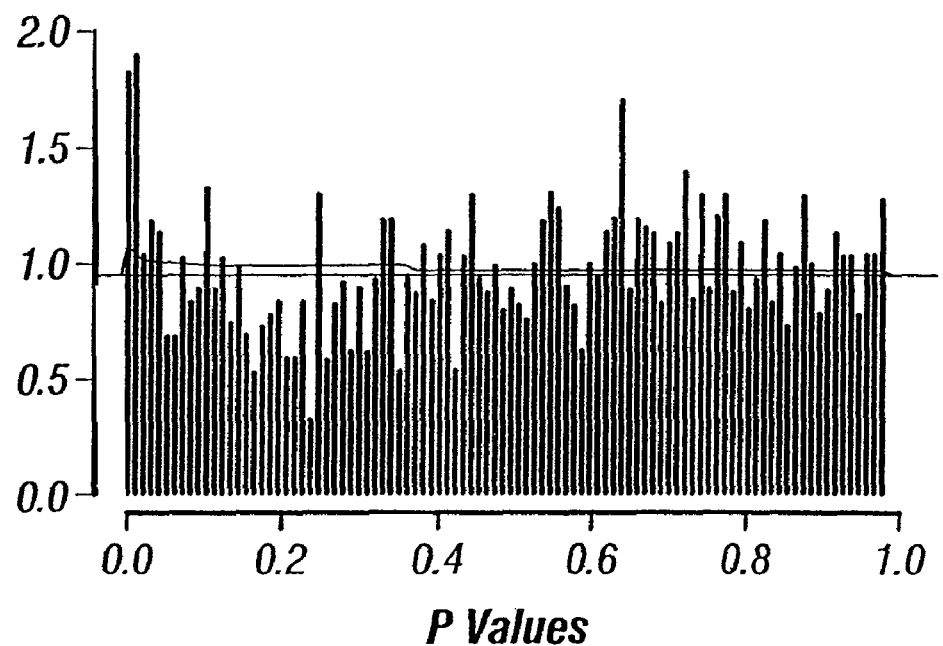
FIG. 9A-D: Analysis of the p-values as a beta-uniform mixture where the transformed peak value (Peak) was added to the Cox model to predict the time from response to therapy to relapse in patients with AML.
Figure 9B:
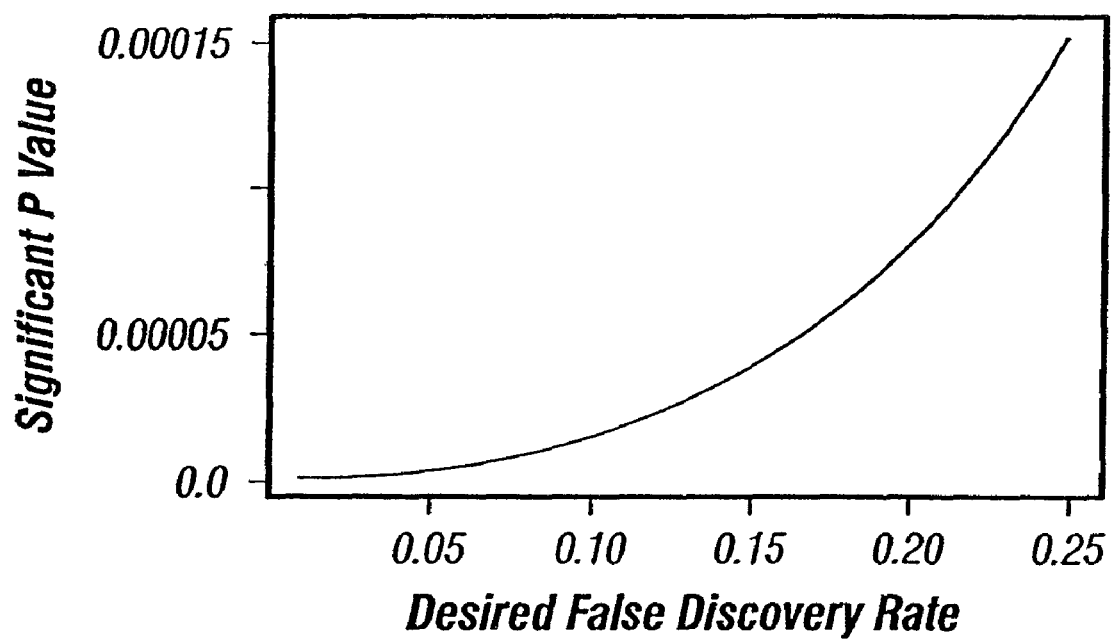
Figure 9C:
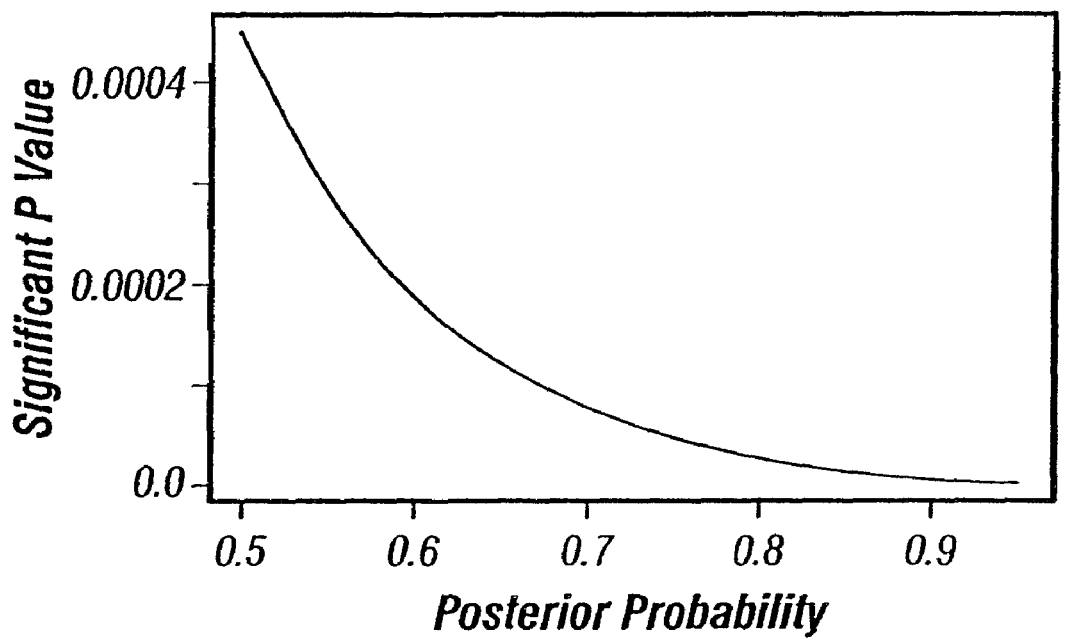
Figure 9D:
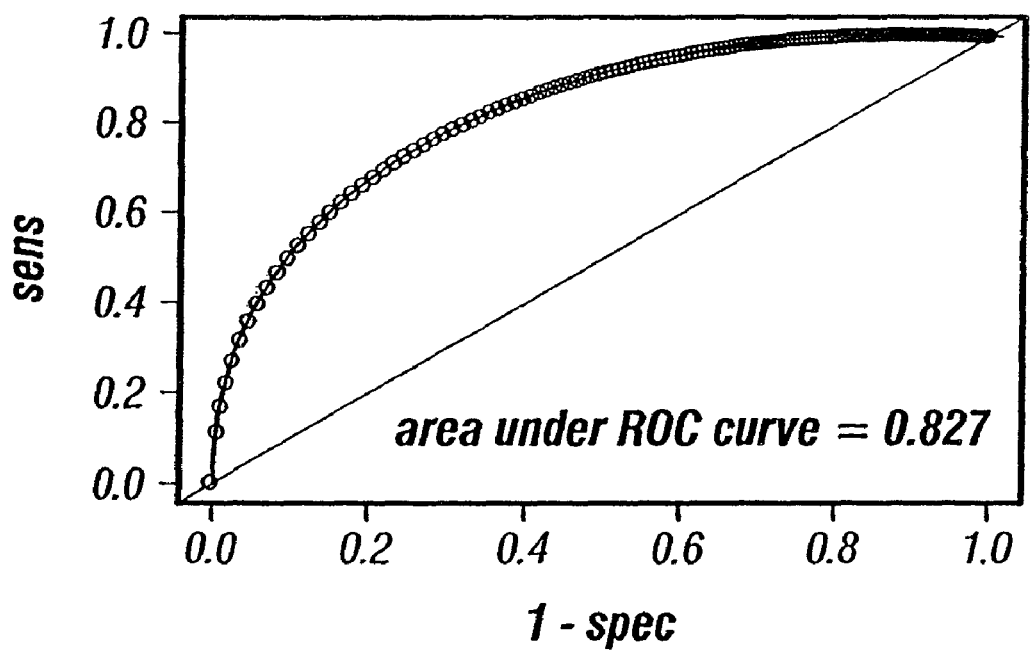
Figure 10A:
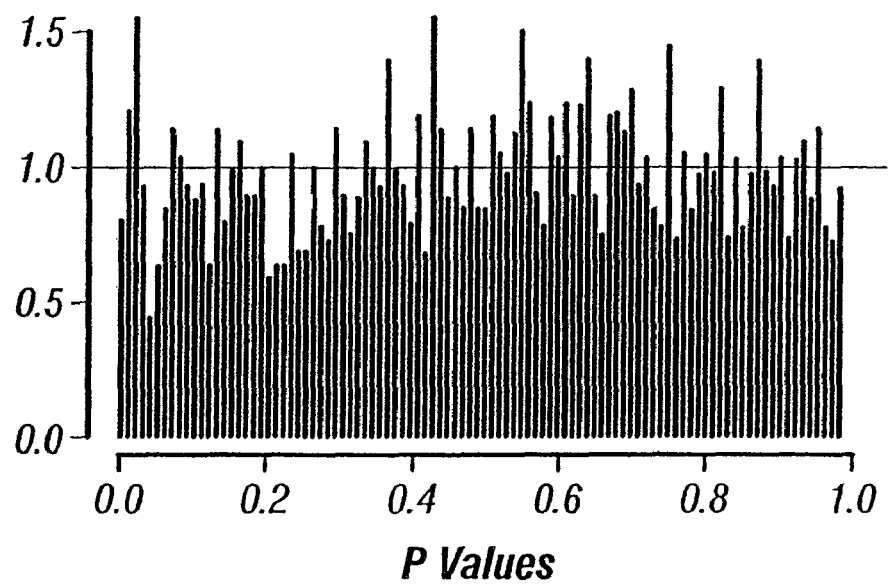
FIG. 10A-D: Analysis of the p-values as a beta-uniform mixture where the transformed peak value (logPeak) was added to the Cox model to predict the time from response to therapy to relapse in patients with AML.
Figure 10B:
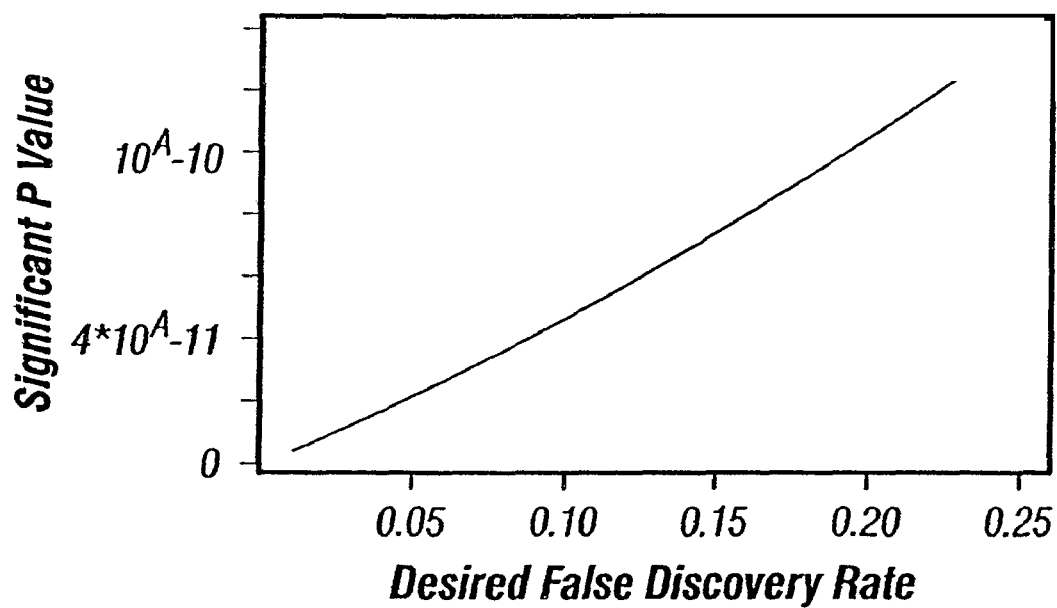
Figure 10C:
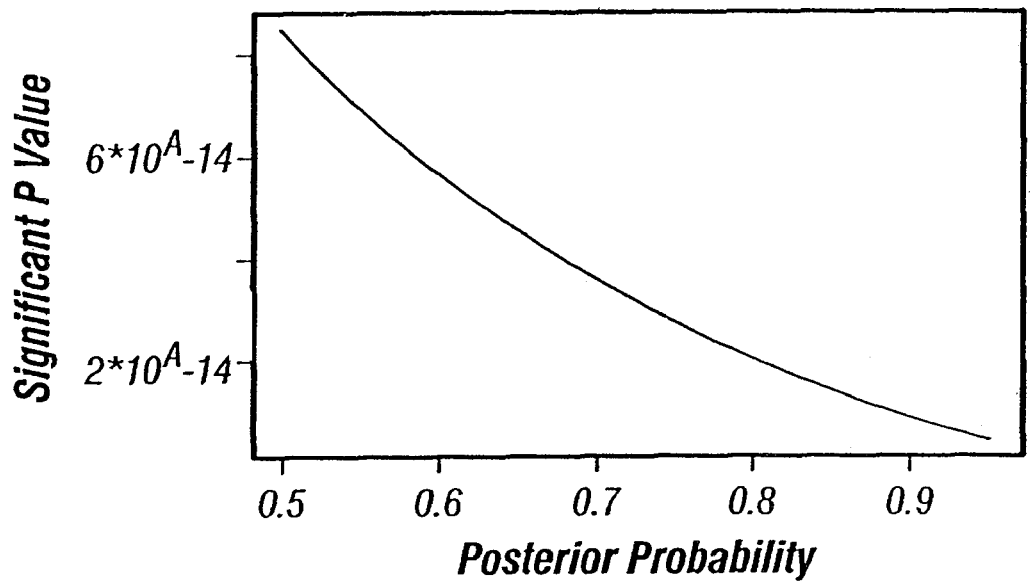
Figure 10D:
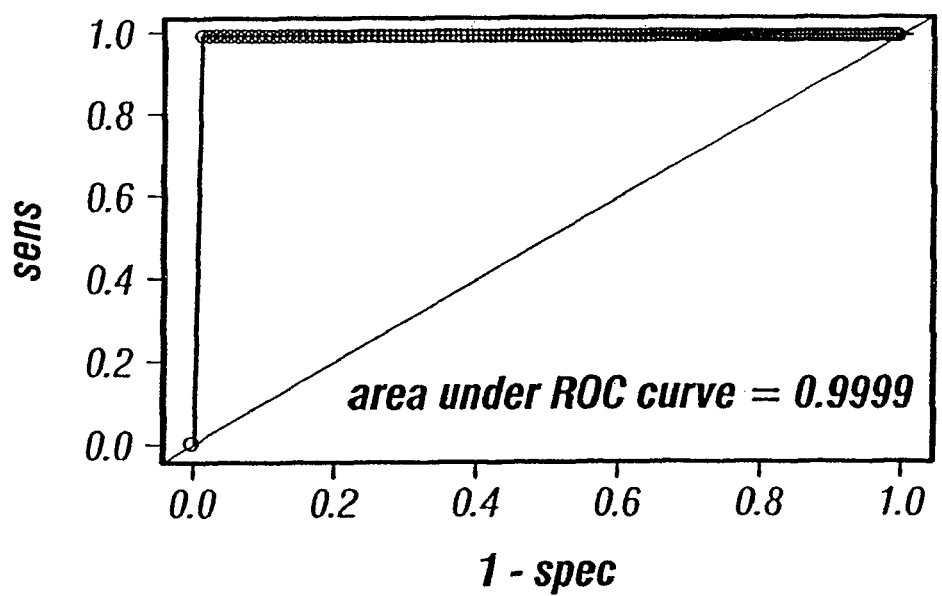

Among patients with hematologic malignancies there can be a highly variable clinical course as reflected by varying survival times and resistance to therapy. Depending on the type of hematologic malignancy a patient has, therapy may include radiation, chemotherapy, bone marrow transplant, biological therapy, or some combination of these therapies. Thus, the accurate diagnosis of a patient's hematologic malignancy is important in determining which therapy option to pursue, as different malignancies respond differently to certain therapies. Even within a particular form of hematologic malignancy (e.g., AML, ALL, CML, CLL) there is significant variability in response to therapy among patients. For example, in acute myeloid leukemia (AML), response to standard chemotherapy (idarubicin+ara-C) varies significantly between patients, with approximately 50% of patients not responding to therapy. Although specific cytogenetic abnormalities in AML patients, such as −5, −7 and 11 q abnormalities, or poor performance status and advanced age are known to be associated with poor response to therapy, accurate prediction of response to therapy remains elusive. The ability to accurately diagnose and predict clinical behavior in patients with hematologic malignancies would allow stratification of patients for therapy options.

Current methods for determining diagnosis or clinical behavior in patients with hematologic malignancies are not reliable and typically depend on one molecule. The present invention enables the evaluation of thousands of proteins at the same time from which a protein profile can be generated that can be used to diagnose or predict clinical behavior in patients with hematologic malignancies. In addition, the invention uses proteomics in combination with blood plasma. Blood plasma is easy to collect and provides the most complex human-derived proteome, making it superior to cells and serum for proteomic studies of hematologic malignancies.

The present invention demonstrates that the diagnosis and prediction of clinical behavior in patients with hematologic malignancies can be accomplished by analysis of proteins present in a plasma sample. Thus, in particular embodiments the present invention uses plasma to create a diagnostic or prognostic protein profile of a hematologic malignancy comprising collecting plasma samples from a population of patients with hematologic malignancies; generating protein spectra from the plasma samples; comparing the protein spectra with clinical data; and identifying protein markers in the plasma samples that correlate with the clinical data. Protein markers identified by this approach can then be used to create a protein profile that can be used to diagnose the hematologic malignancy or determine the prognosis of the hematologic malignancy. In some embodiments, protein markers may be identified by comparing the protein profile from patients with hematologic malignancies with protein profiles from unaffected individuals.

Using the methods of the invention, those skilled in the art will be able to identify protein markers that can accurately diagnose hematologic malignancies, predict a patient's response to therapy, predict a patient's time to relapse, and predict a patient's survival time. Furthermore, the invention provides several protein markers shown to accurately predict response to therapy in patients with AML, as well as several protein markers shown to accurately predict the time to relapse in patients with AML.

B. The Plasma Proteome

Blood plasma is easy to collect and provides the most complex human-derived proteome, containing other tissue proteomes as subsets. The protein content of plasma can be classified into the following groups: proteins secreted by solid tissues and that act in the plasma; immunoglobulins; "long distance" receptor ligands; "local" receptor ligands, temporary passengers; tissue leakage products; aberrant secretions from cancer cells and other diseased cells; and foreign proteins (Anderson and Anderson, 2002).

Other body fluids including cerebrospinal fluid, synovial fluid, and urine share some of the protein content with plasma.

These samples, however, are more difficult to obtain in a useful state than plasma. For example, collection of cerebrospinal fluid and synovial fluid are invasive procedures that can be painful and involve some risk, while processing urine to a useful sample for protein analysis can be difficult in a clinical setting. Blood plasma, however, may be easily collected by venipuncture. For example, venous blood samples can be drawn and collected in sterile ethylene diamine tetra acetate (EDTA) tubes. The plasma can then be separated by centrifugation. If desired, the plasma may be stored at −70° C. for later analysis.

Characterizing the proteins in plasma can be challenging due to the large amount of albumin present and the wide range in abundance of other proteins. The present invention, however, shows that proteomics in combination with plasma can provide a reliable approach to diagnosing hematologic malignancies and predicting clinical behavior in patient's with hematologic malignancies.

C. Protein Analysis

The present invention employs methods of separating proteins from plasma. Methods of separating proteins are well known to those of skill in the art and include, but are not limited to, various kinds of chromatography (e.g., anion exchange chromatography, affinity chromatography, sequential extraction, and high performance liquid chromatography) and mass spectrometry. The separation and detection of the proteins in a plasma sample generates a protein spectra for that sample.

1. Mass Spectrometry

In preferred embodiments the present invention employs mass spectrometry. Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). Mass spectrometry (MS), because of its extreme selectivity and sensitivity, has become a powerful tool for the quantification of a broad range of bioanalytes including pharmaceuticals, metabolites, peptides and proteins.

Of particular interest in the present invention is surface-enhanced laser desorption ionization-time of flight mass spectrometry (SELDI-TOF MS). Whole proteins can be analyzed by SELDI-TOF MS, which is a variant of MALDI-TOF (matrix-assisted desorption ionization-time of flight) mass spectrometry. In SELDI-TOF MS, fractionation based on protein affinity properties is used to reduce sample complexity. For example, hydrophobic, hydrophilic, anion exchange, cation exchange, and immobilized-metal affinity surfaces can be used to fractionate a sample. The proteins that selectively bind to a surface are then irradiated with a laser. The laser desorbs the adherent proteins, causing them to be launched as ions. The "time of flight" of the ion before detection by an electrode is a measure of the mass-to-charge ration (m/z) of the ion. The SELDI-TOF MS approach to protein analysis has been implemented commercially (e.g., Ciphergen).

2. Two-Dimensional Electrophoresis

In certain embodiments the present invention employs high-resolution electrophoresis to separate proteins from a biological sample such as plasma. Preferably, two-dimensional gel electrophoresis is used to generate a two-dimensional array of spots of proteins from a sample.

Two-dimensional electrophoresis is a useful technique for separating complex mixtures of molecules, often providing a much higher resolving power than that obtainable in one-dimension separations. Two-dimensional gel electrophoresis can be performed using methods known in the art (See, e.g., U.S. Pat. Nos. 5,534,121 and 6,398,933). Typically, proteins in a sample are separated by, e.g., isoelectric focusing, during which proteins in a sample are separated in a pH gradient until they reach a spot where their net charge is zero (i.e., isoelectric point). This first separation step results in one-dimensional array of proteins. The proteins in one dimensional array is further separated using a technique generally distinct from that used in the first separation step. For example, in the second dimension, proteins separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass of the protein.

Proteins in the two-dimensional array can be detected using any suitable methods known in the art. Staining of proteins can be accomplished with colorimetric dyes (coomassie), silver staining and fluorescent staining (Ruby Red). As is known to one of ordinary skill in the art, spots/or protein profiling patterns generated can be further analyzed for example, by gas phase ion spectrometry. Proteins can be excised from the gel and analyzed by gas phase ion spectrometry. Alternatively, the gel containing proteins can be transferred to an inert membrane by applying an electric field and the spot on the membrane that approximately corresponds to the molecular weight of a marker can be analyzed by gas phase ion spectrometry.

3. Other Methods of Protein Analysis

In addition to the methods described above, other methods of protein separation known to those of skill in the art may be useful in the practice of the present invention. The methods of protein analysis may be used alone or in combination.

a. Chromatography

Chromatography is used to separate organic compounds on the basis of their charge, size, shape, and solubilities. A chromatography consists of a mobile phase (solvent and the molecules to be separated) and a stationary phase either of paper (in paper chromatography) or glass beads, called resin, (in column chromatography) through which the mobile phase travels. Molecules travel through the stationary phase at different rates because of their chemistry. Types of chromatography that may be employed in the present invention include, but are not limited to, high performance liquid chromatography (HPLC), ion exchange chromatography (IEC), and reverse phase chromatography (RP). Other kinds of chromatography include: adsorption, partition, affinity, gel filtration and molecular sieve, and many specialized techniques for using them including column, paper, thin-layer and gas chromatography (Freifelder, 1982).

i. High Performance Liquid Chromatography

High performance liquid chromatography (HPLC) is similar to reverse phase, only in this method, the process is conducted at a high velocity and pressure drop. The column is shorter and has a small diameter, but it is equivalent to possessing a large number of equilibrium stages.

Although there are other types of chromatography (e.g., paper and thin layer), most applications of chromatography employ a column. The column is where the actual separation takes place. It is usually a glass or metal tube of sufficient strength to withstand the pressures that may be applied across it. The column contains the stationary phase. The mobile phase runs through the column and is adsorbed onto the stationary phase. The column can either be a packed bed or open tubular column. A packed bed column is comprised of a stationary phase which is in granular form and packed into the column as a homogeneous bed. The stationary phase completely fills the column. An open tubular column's stationary phase is a thin film or layer on the column wall. There is a passageway through the center of the column.

The mobile phase is comprised of a solvent into which the sample is injected. The solvent and sample flow through the column together; thus the mobile phase is often referred to as the "carrier fluid." The stationary phase is the material in the column for which the components to be separated have varying affinities. The materials which comprise the mobile and stationary phases vary depending on the general type of chromatographic process being performed. The mobile phase in liquid chromatography is a liquid of low viscosity which flows through the stationary phase bed. This bed may be comprised of an immiscible liquid coated onto a porous support, a thin film of liquid phase bonded to the surface of a sorbent, or a sorbent of controlled pore size.

High-performance chromatofocusing (HPCF) produces liquid pI fractions as the first-dimension of protein separation followed by high-resolution reversed-phase (RP) HPLC of each of the pI fractions as the second dimension. Proteins are now mapped (like gels), but the liquid fractions make for easy interface with mass spectrometry (MS) for detailed intact protein characterization and identification (unlike gels) on more selective basis without resorting to protein digestion.

ii. Reversed-Phase Chromatography

Reversed phase chromatography (RPC) utilizes solubility properties of the sample by partitioning it between a hydrophilic and a lipophilic solvent. The partition of the sample components between the two phases depends on their respective solubility characteristics. Less hydrophobic components end up primarily in the hydrophilic phase while more hydrophobic ones are found in the lipophilic phase. In RPC, silica particles covered with chemically-bonded hydrocarbon chains (2-18 carbons) represent the lipophilic phase, while an aqueous mixture of an organic solvent surrounding the particle represents the hydrophilic phase.

When a sample component passes through an RPC column the partitioning mechanism operates continuously. Depending on the extractive power of the eluent, a greater or lesser part of the sample component will be retained reversibly by the lipid layer of the particles, in this case called the stationary phase. The larger the fraction retained in the lipid layer, the slower the sample component will move down the column. Hydrophilic compounds will move faster than hydrophobic ones, since the mobile phase is more hydrophilic than the stationary phase.

Compounds stick to reverse phase HPLC columns in high aqueous mobile phase and are eluted from RP HPLC columns with high organic mobile phase. In RP HPLC compounds are separated based on their hydrophobic character. Peptides can be separated by running a linear gradient of the organic solvent.

Along with the partitioning mechanism, adsorption operates at the interface between the mobile and the stationary phases. The adsorption mechanism is more pronounced for hydrophilic sample components while for hydrophobic ones the liquid-liquid partitioning mechanism is prevailing. Thus the retention of hydrophobic components is greatly influenced by the thickness of the lipid layer. An 18 carbon layer is able to accommodate more hydrophobic material than an 8 carbon or a 2 carbon layer.

The mobile phase can be considered as an aqueous solution of an organic solvent, the type and concentration of which determines the extractive power. Some commonly used organic solvents, in order of increasing hydrophobicity are: methanol, propanol, acetonitrile, and tetrahydrofuran.

Due to the very small sizes of the particles employed as the stationary phase, very narrow peaks are obtained. In some embodiments, reverse phase HPLC peaks are represented by bands of different intensity in the two-dimensional image, according to the intensity of the peaks eluting from the HPLC. In some instances, peaks are collected as the eluent of the HPLC separation in the liquid phase. To improve the chromatographic peak shape and to provide a source of protons in reverse phase chromatography acids are commonly used. Such acids are formic acid, trifluoroacetic acid, and acetic acid.

iii. Ion Exchange Chromatography

Ion exchange chromatography (IEC) is applicable to the separation of almost any type of charged molecule, from large proteins to small nucleotides and amino acids. It is very frequently used for proteins and peptides, under widely varying conditions. In protein structural work the consecutive use of gel permeation chromatography (GPC) and IEC is quite common.

In ion exchange chromatography, a charged particle (matrix) binds reversibly to sample molecules (proteins, etc.). Desorption is then brought about by increasing the salt concentration or by altering the pH of the mobile phase. Ion exchange containing diethyl aminoethyl (DEAE) or carboxymethyl (CM) groups are most frequently used in biochemistry. The ionic properties of both DEAE and CM are dependent on pH, but both are sufficiently charged to work well as ion exchangers within the pH range 4 to 8 where most protein separations take place.

The property of a protein which govern its adsorption to an ion exchanger is the net surface charge. Since surface charge is the result of weak acidic and basic groups of protein; separation is highly pH dependent. Going from low to high pH values the surface charge of proteins shifts from a positive to a negative charge surface charge. The pH versus net surface curve is a individual property of a protein, and constitutes the basis for selectivity in IEC.

As in all forms of liquid chromatography, conditions are employed that permit the sample components to move through the column with different speeds. At low ionic strengths, all components with affinity for the ion exchanger will be tightly adsorbed at the top of the ion exchanger and nothing will remain in the mobile phase. When the ionic strength of the mobile phase is increased by adding a neutral salt, the salt ions will compete with the protein and more of the sample components will be partially desorbed and start moving down the column. Increasing the ionic strength even more causes a larger number of the sample components to be desorbed, and the speed of the movement down the column will increase. The higher the net charge of the protein, the higher the ionic strength needed to bring about desorption. At a certain high level of ionic strength, all the sample components are fully desorbed and move down the column with the same speed as the mobile phase. Somewhere in between total adsorption and total desorption one will find the optimal selectivity for a given pH value of the mobile phase. Thus, to optimize selectivity in ion exchange chromatography, a pH value is chosen that creates sufficiently large net charge differences among the sample components. Then, an ionic strength is selected that fully utilizes these charge differences by partially desorbing the components. The respective speed of each component down the column will be proportional to that fraction of the component which is found in the mobile phase.

Very often the sample components vary so much in their adsorption to the ion exchanger that a single value of the ionic strength cannot make the slow ones pass through the column in a reasonable time. In such cases, a salt gradient is applied to bring about a continuous increase of ionic strength in the mobile phase.

D. Analysis of Protein Markers

1. Extraction of Protein Marker Locations

Following the generation of protein spectra by, for example, SELDI-TOF MS, protein markers are identified for further analysis. Protein marker detection can be made easier by reducing the background noise. The background noise can be reduced at different levels. One method of reducing background noise is to average the raw protein spectra data. First, peaks should be normalized to assure that equal amounts of samples are compared. There are several methods for normalization known to those skilled in the art. A common approach is normalizing according to intensity: Total Ion Current, height, area, or mass. A different method for normalization is using the following formula (I=intensity):

$$\text{Normalized } I = \text{Current} I - \text{Minimum} I / \text{Maximum} I - \text{minimum} I$$

After normalization, reducing background can be achieved by eliminating peaks that are not seen in majority (50-70%) of samples.

Systems for mass spectra acquisition are commercially available. One example is the Ciphergen ProteinChip® Reader (Ciphergen Biosystems, Inc.). The chip reader may be used with peak detection software such as CiphergenExpress 3.0. This software calculates clusters by determining peaks that are above a given signal-to-noise ratio, and that are present in multiple spectra. Various settings for noise subtraction, peak detection, and cluster completion may be evaluated to optimize the analysis. For example, a first pass peak detection of 5.0 signal-to-noise on both peaks and valleys, and a cluster completion window of 1.0 times peak width, with a second pass signal-to-noise setting of 2.0 for both peaks and valleys may be used.

The use of total ion current as a normalization factor is a common practice in SELDI data analysis; however, other methods of normalization may be used. For example, normalization could be done using the peak ratio approach in which the ratios of peaks near each other (e.g., within 5 peaks upstream and downstream) are used for normalizing. The peak ratio approach has an additional advantage of possibly detecting post-translational modifications more effectively.

Peaks may also be detected manually. The results of manual peak detection may then be analyzed using software, such as Matlab (MathWorks, Natick, Mass.), followed by decision tree analysis. A non-limiting example of decision tree analysis software is CART from Salford Systems, which is implemented in Biomarker Patterns Software 4.0 from Ciphergen Biosystems, Inc.

Replicate samples can be analyzed to confirm the reproducibility of the protein spectra generated according to the methods of the invention. Those of skill in the art are familiar with statistical methods that can be used to determine the reproducibility of the analysis. For example, an agglomerative clustering algorithm may be used to show that replicate samples cluster as nearest neighbors, thus confirming reproduciblitiy. Agglomerative clustering analysis is the searching for groups in the data in such a way that objects belonging to the same cluster resemble each other. The computer analysis proceeds by combining or dividing existing groups, producing a hierarchical structure displaying the order in which groups are merged or divided. Agglomerative methods start with each observation in a separate group and proceed until all observations are in a single group.

2. Determining the Relevance of Protein Markers

To test the relevance of the protein markers identified in the protein spectra, various methods of statistical analysis known to those of skill in the art may be employed. For example, a univariate model, multivariate model, or hierarchical cluster analysis may be used.

a. Multivariate Modeling

A multivariate model is a model that aims to predict or explain the behavior of a dependent variable on the basis of a set of known independent variables. The purpose of using multivariate analysis is to demonstrate that the proteomic analysis as a variable in predicting response, survival, and duration of response is independent from the currently known variables that can predict the same thing. If the proteomic data adds to the model that includes the conventional markers, the p-value will be significant, but if the proteomic data does not add to the model and similar prediction can be achieved using other conventional markers, the p-value will not be significant even if it was significant in univariate analysis.

For predicting a the response to therapy of a patient with a hematologic malignancy, a multivariate model is preferred. An example of a multivariate model for predicting response to therapy in a patient with AML is (Response~Cytogenetics+Performance.Status+Age).

Cytogenetic findings represent the chromosomal abnormalities that were found in the tumor cells. Dependent on these abnormalities, the leukemia/tumor can be classified as good, intermediate, or bad. For example, in a patient with AML and cytogenetic abnormalities including deletion of chromosome 5 or 7 or abnormalities on chromosome 11, this patient has a "bad" disease (>90% die within one year and will not respond to therapy). Patients with AML and t(8;21), t(15;17), or Inv 16 are classified as "good" disease and the rest are with "intermediate" disease.

With regard to age, the older the patient the worse the disease (continuous variable). Patients >65 years old are classified with "bad" disease.

Performance status is a scoring system to evaluate the patient's overall health as described below in Table 5. Obviously, the higher the grade (ECOG), the less likely the patient will survive.

TABLE 5

Performance Status Criteria.

| ECOG Performance Status Scale | | Karnofsky Performance Scale | |
| --- | --- | --- | --- |
| Grade | Descriptions | Percent | Description |
| 0 | Normal activity. Fully active, able to carry on all pre-disease performance without restriction. | 100 | Normal, no complaints, no evidence of disease. |
|  |  | 90 | Able to carry on normal activity; minor signs or symptoms of disease. |

TABLE 5-continued

Performance Status Criteria.

| ECOG Performance Status Scale | | Karnofsky Performance Scale | |
| --- | --- | --- | --- |
| Grade | Descriptions | Percent | Description |
| 1 | Symptoms, but ambulatory. Restricted in physically strenuous activity, but ambulatory and able to carry out work of a light or sedentary nature (e.g., light housework, office work). | 80 | Normal activity with effort; some signs or symptoms of disease. |
| | | 70 | Cares for self, unable to carry on normal activity or to do active work. |
| 2 | In bed <50% of the time. Ambulatory and capable of all self-care, but unable to carry out any work activities. Up and about more than 50% of waking hours. | 60 | Requires occasional assistance, but is able to care for most of his/her needs. |
| | | 50 | Requires considerable assistance and frequent medical care. |
| 3 | In bed >50% of the time. Capable of only limited self-care, confined to bed or chair more than 50% of waking hours. | 40 | Disabled, requires special care and assistance. |
| | | 30 | Severely disabled, hospitalization indicated. Death not imminent. |
| 4 | 100% bedridden. Completely disabled. Cannot carry on any self-care. Totally confined to bed or chair. | 20 | Very sick, hospitalization indicated. Death not imminent. |
| | | 10 | Moribund, fatal processes progressing rapidly. |
| 5 | Dead. | 0 | Dead. |

To test the relevance of a specific protein marker to the prediction of a behavior, the protein marker can be added to the multivariate model. For example, the value (i.e., height) of a protein peak identified by SELDI MS can be added to the base multivariate model for predicting response to therapy in a patient with AML to give the extended multivariate model of (Response~Cytogenetics+Performance.Status+Age+Peak Info) where Peak Info is information from a given peak. Preferably Peak Info is a transformed peak value, such as logPeak, logPeak+(logPeak)$^2$, Peak+Peak$^2$, or Peak+log-Peak.

After applying the peak value to the multivariate model, a p-value is produced. Those of skill in the art are familiar with methods of calculating p-values. For example, a p-value may be determined by applying ANOVA (analysis of variance between groups) on the base multivariate model and the extended multivariate model.

To adjust for multiple testing a beta-uniform mixture analysis may be used. The p-value is considered significant only if it is less than the cut-off as determined by the beta-uniform mixture analysis, in which the transformation is confirmed to be unique and not uniform. This adjusts for the multiple testing.

b. Cox Model

Those of skill in the art are familiar with the Cox proportional hazards model, which is a commonly used regression model for analyzing data points with time, such as survival, time to progression, time to relapse, or time to therapy. The Cox model allows the estimation of nonparametric survival (or other event of interest) curves (such as Kaplan-Meier curves) in the presence of covariates. This can be performed with continuous or as dichotomized variables. The effect of the covariates upon survival is usually of primary interest. The Cox model can also be performed in the context of multivariate analysis by incorporating several variables. In the multivariate model, the analysis will first analyze the first variable, then analyze the second variable in the groups generated from the first variable and so on.

In one embodiment of the invention, protein peak values were fitted to the Cox model:

$$h(t)=h_0(t)\exp(\beta \cdot f(\text{Peak})),$$

where h(t) is the hazard at time t, $h_0$(t) is the baseline hazard, and f(Peak) is some transformation of the peak value. When the Cox model was applied to predict time to relapse, the "hazard" was relapse, and the "baseline hazard" was the risk of relapsing based on variables other than peak value. Resulting p-values may be analyzed by means of a beta-uniform mixture analysis. A positive value of the coefficient β means that an increased peak height corresponds to increased risk of relapse. The p-value was considered significant only if it is less than the cut-off as determined by the beta-uniform mixture analysis, in which the transformation is confirmed to be unique and not uniform. This adjusts for the multiple testing.

In addition to the analyses described herein, many additional questions can be asked using the Cox model. For example, the data can be used to predict patients who will have fungal infection, or patients who would die in the first two weeks. Similar statistical analysis can be used to determine response to second therapy after relapsing c. Decision Tree Algorithm In one embodiment of the present invention, a decision tree algorithm was used to identify protein spectra useful for predicting clinical outcome (e.g., responders versus non-responders). CART software from Salford Systems is one example of a commercially available decision tree tool. CART automatically sifts large, complex databases, searching for and isolating significant patterns and relationships. This information can then be used to generate predictive models. Variables that may be included in the analysis along with peak values and peak ratios include clinical outcome, patient demographics, and cellular analysis. When using decision trees, caution must be exercised to prevent overfitting (Wiemer and Prokudin 2004). When approach to limiting overfitting is to limit the number of levels allowed. For example, the number of levels may be limited to two, meaning that the model could only be comprised of at most two variables from the set of all peak values and all observational variables (e.g., clinical outcomes, patient demographics, cellular analysis).

E. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Using Proteomics to Predict Response to Therapy in Patients with Acute Myeloid Leukemia In acute myeloid leukemia (AML), response to standard chemotherapy (idarubicin+ara-C) varies significantly between patients and approximately 50% of the patients do not respond to therapy. Although specific cytogenetic abnormalities in AML patients, such as −5, −7 and 11 q abnormalities, or poor performance status and advanced age are known to be associated with poor response to therapy, accurate prediction of response to therapy remains elusive. Accurate prediction of response to therapy in AML may allow stratification of patients and the use of different regimens that might prove to be more effective in these patients when used upfront before compromising the patient's immune system with conventional therapy that will not be adequate to induce remission. Recent advances in genomics and proteomics have provided new hope for finding new molecular markers for the prediction of response to chemotherapy in AML.

The inventors explored the potential of using proteomics in predicting response to standard chemotherapy (idarubicin+ara-C) in acute myeloid leukemia (AML). Using surface-enhanced laser desorption/ionization (SELDI) mass spectrometry, the inventors analyzed protein profiles in the pre-treatment plasma from patients with AML and used these profiles for the prediction of response to therapy.

Plasma samples were obtained prior to initial cytotoxic therapy from 90 patients with a diagnosis of AML seen at the University of Texas M.D. Anderson Cancer Center. Patients were selected randomly. Forty patient samples were used in the testing set to build the model; the remaining 50 patient samples were used in the validation set to test the accuracy and validity of the model. Diagnosis was based on morphologic, cytochemical staining, immunophenotypic analysis (CD64, CD13, CD33, CD14, CD117, CD10, CD19, CD3, DR, and Tdt), and molecular analysis as indicated. Cytogenetic analysis was also performed. Patients were treated according to Institutional Review Board-approved clinical research protocols at M.D. Anderson Cancer Center after signing informed consent. Ten milliliters of peripheral venous blood samples were collected in sterile EDTA tubes. Plasma was separated by centrifugation at 1500 g for 10 minutes in a refrigerated centrifuge and stored at −70° C. Plasma samples from normal individuals were used as controls on each chip.

Plasma proteins were first enriched and fractionated into 4 different fractions according to pH using strong anion exchange resin (Fraction1=pH9,pH7, Fraction2=pH5, Fraction3=pH4, Fraction4=pH3, organic). Each fraction was then immobilized on three arrays: anion exchange (SAX), cation exchange (WCX), and metal affinity chip (IMAC). Chips were read on Ciphergen reader Model PBS II. Spectra from plasma samples corresponding to 40 patients were collected from each fraction and surface (for a total of 12 spectra per patient) and peaks were compared.

The peak locations were extracted using the following approach. For each surface and fraction, the inventors averaged all raw spectra. This reduced the noise significantly and made peak detection easier and more robust. This way the inventors applied the peak detection algorithm to 12 average spectra. These peaks were filtered with respect the estimated Signal to Noise ratio (S/N) in their vicinity in the average spectra. In particular the inventors used S/N>5.

Within a fraction, the locations of the peaks (mass values) are the same for all spectra. Only the heights of the peaks changed across the various spectra. The total number of peaks from all surfaces and fractions was 1976.

The inventors inspected numerous individual spectra (as well as average spectra for all 12 Surface-Fraction combinations) from both testing and validation sets to detect cases of poor alignment. There were no problems in alignment, thus the extracted peak heights from validation set at the 1976 locations were similar to the testing set. Each sample was analyzed in duplicate and an agglomerative clustering algorithm showed that replicate samples cluster as nearest neighbors, confirming the reproducibility of the analysis.

Known variables that influence patient survival include cytogenetics, performance status, and age. As expected, multivariate modeling demonstrated that age, cytogenetics, and performance status are strong predictors of response to therapy. To test the relevance of the protein peaks detected in the analysis, the inventors added one peak at a time to the base model (Response~Cytogenetics+Performance.Status+Age) and produced a p-value by applying ANOVA on the base and extended models. The extended model is: (Response~Cytogenetics+Performance.Status+Age+Peak Info), where Peak Info is additional info from a given peak.

The inventors added to the base model the following transformed peak values:
(i) logPk (1 d.o.f.)
(ii) logPk+(logPk)$^2$ (2 d.o.f.)
(iii) Pk+Pk$^2$ (2 d.o.f.)
(iv) Pk+logPk (2 d.o.f.)

For each case, a set of p-values was obtained and used for a beta-uniform analysis. The results from the beta-uniform mixture analysis of case (i), (ii), (iii), and (iv) are shown in FIG. 1, FIG. 2, FIG. 3, and FIG. 4, respectively. The threshold for the p-values was calculated after the beta-uniform mixture analysis by fixing the false discovery rate (FDR). For case (i) the FDR was set to 0.2, for cases (ii), (iii), and (iv) FDR was set to 0.1. The most significant peaks for cases (i), (ii), (iii), and (iv) are shown in FIG. 5, FIG. 6, FIG. 7, and FIG. 8, respectively.

An important question is how many peaks have to be included in the regression model to completely predict the response. It turns out that for the four different cases the inventors examined, a small number of peaks suffice. The base model (Response~Cytogenetics+Performance.Status+Age) accurately predicted the response in 31 out of 40 patients. The base model predicted 21 no response (NR) and 19 complete response (CR). Of these, there were 5 false NR and 4 false CR. The base model was extended by adding the most significant peaks identified for cases (i), (ii), (iii), and (iv). In each of FIGS. 5-8, the 3rd column shows the number of false predictions (F.P.) of the base model extended with each individual peak.

In addition to adding the individual peaks to the model, all possible pairs of peaks were also added to the model. For case (i) no pair of peaks could predict the response to therapy with fewer than 3 false predictions. However, for cases (ii), (iii), and (iv) there were several pairs of peaks that can perfectly predict response to therapy when added to the regression model. Table 6 shows the significant peaks for case (ii). For case (ii), 42 pairs of peaks could predict response perfectly when added to the base model. For example, the first two protein peaks (shaded) in Table 6 were a pair that perfectly predicted response. Table 7 shows the significant peaks for case (iii). For case (iii), 89 pairs of peaks could predict response perfectly when added to the base model. For example, the first and third protein peaks (shaded) in Table 7 were a pair that perfectly predicted response. Table 8 shows the significant peaks for case (iv). For case (iv), 52 pairs of peaks could predict response perfectly when added to the base model. For example, the first two protein peaks (shaded) in Table 8 were a pair that perfectly predicted response.

TABLE 6

| Surface.Fraction | M/Z |
| --- | --- |
| IMAC3-Fraction1 | 2533.253 |
| SAX2-Fraction2 | 12801.17 |
| SAX2-Fraction3 | 944.0915 |
| WCX2-Fraction3 | 11095.88 |
| IMAC3-Fraction1 | 2648.984 |
| SAX2-Fraction2 | 13506.15 |
| WCX2-Fraction2 | 12687.09 |
| SAX2-Fraction2 | 12519.29 |
| WCX2-Fraction4 | 207.8056 |
| SAX2-Fraction3 | 40019.19 |
| WCX2-Fraction2 | 12241.71 |
| WCX2-Fraction2 | 26397.83 |
| IMAC3-Fraction1 | 3223.238 |
| IMAC3-Fraction2 | 895.5696 |
| IMAC3-Fraction1 | 2675.053 |
| SAX2-Fraction2 | 518.8676 |
| SAX2-Fraction3 | 876.7685 |

TABLE 7

| Surface.Fraction | M/Z |
| --- | --- |
| IMAC3-Fraction1 | 2533.253 |
| IMAC3-Fraction2 | 895.5696 |
| SAX2-Fraction2 | 12801.17 |
| WCX2-Fraction3 | 11095.877 |
| SAX2-Fraction2 | 13506.152 |
| IMAC3-Fraction1 | 2648.9839 |
| SAX2-Fraction3 | 40019.188 |
| WCX2-Fraction2 | 26397.831 |
| WCX2-Fraction3 | 15269.208 |
| SAX2-Fraction2 | 12519.29 |
| SAX2-Fraction2 | 16424.507 |
| IMAC3-Fraction1 | 2509.4679 |
| SAX2-Fraction2 | 8330.8957 |
| SAX2-Fraction2 | 518.8676 |
| IMAC3-Fraction1 | 2274.7727 |
| SAX2-Fraction3 | 944.0915 |
| IMAC3-Fraction1 | 3223.2382 |
| WCX2-Fraction3 | 22130.579 |
| WCX2-Fraction4 | 207.8056 |
| IMAC3-Fraction4 | 9925.4222 |

TABLE 7-continued

| Surface.Fraction | M/Z |
| --- | --- |
| IMAC3-Fraction1 | 5076.1814 |
| SAX2-Fraction3 | 353.8245 |
| WCX2-Fraction2 | 14616.859 |
| SAX2-Fraction3 | 8127.5061 |
| WCX2-Fraction4 | 226.097 |
| IMAC3-Fraction1 | 2675.0528 |
| SAX2-Fraction3 | 6873.2851 |

TABLE 8

| Surface.Fraction | M/Z |
| --- | --- |
| IMAC3-Fraction1 | 2533.253 |
| SAX2-Fraction2 | 12801.17 |
| WCX2-Fraction3 | 11095.88 |
| IMAC3-Fraction1 | 2648.984 |
| SAX2-Fraction3 | 944.0915 |
| SAX2-Fraction2 | 13506.15 |
| IMAC3-Fraction2 | 895.5696 |
| SAX2-Fraction2 | 12519.29 |
| SAX2-Fraction3 | 40019.19 |
| WCX2-Fraction2 | 26397.83 |
| WCX2-Fraction4 | 207.8056 |
| IMAC3-Fraction1 | 3223.238 |
| WCX2-Fraction2 | 12687.09 |
| SAX2-Fraction2 | 518.8676 |
| WCX2-Fraction3 | 15269.21 |
| SAX2-Fraction2 | 16424.51 |
| SAX2-Fraction2 | 8330.896 |
| IMAC3-Fraction1 | 2675.053 |
| IMAC3-Fraction1 | 2509.468 |
| WCX2-Fraction2 | 12241.71 |
| IMAC3-Fraction4 | 9925.422 |
| WCX2-Fraction3 | 22130.58 |

This data suggests that proteomic profiling is useful in predicting clinical behavior in AML patients. This approach may be useful in stratifying patients for specific therapy options.

Example 2

Using Proteomics to Predict Time from Response to Relapse in Patients with Acute Myeloid Leukemia The inventors processed spectra produced from plasma samples collected from 42 and 48 patients with AML. For each patient the inventors have 24 spectra coming from 4 different fractions (Fraction1=pH9,pH7, Fraction2=pH5, Fraction3=pH4, Fraction4=pH3, organic), 3 surfaces (IMAC3—$Cu^{++}$, SAX2, WCX2) and duplication of the experiments.

The first set of spectra (from 42 patients) was produced in the second half of February, 2003. The second set (from 48 subjects) was produced at the end of June, 2003. The following analysis applies to all spectra corresponding to 40 patients from Set 1 and 42 patients from Set 2. The remaining spectra were discarded due to missing clinical information.

There are 36 patients that responded to the treatment between the two sets (19 from Set 1 and 17 from Set 2). Among them, 17 patients relapsed during the study (5 in Set 1 and 12 in Set 2).

After processing the spectra, the inventors extracted the heights of 1976 peaks. For each peak, the inventors fitted the Cox model:

$$h(t)=h_0(t)\exp(\beta \cdot f(\text{Peak})),$$

where h(t) is the hazard at time t, $h_0(t)$ is the baseline hazard, and f(Peak) is some transformation of the peak value. The inventors examined two cases: f(Peak)=Peak and f(Peak)=logPeak.

First Case: Using the Peak Height to Fit the Cox Model.

For each one of the 1976 peaks the inventors fitted a Cox proportional hazards model. The resulting p-values were analyzed by means of a beta-uniform mixture (BUM). FIG. 9 shows the distribution of p-values. Table 9 shows the peaks, in order of significance (ascending order of p-values). The third column of Table 9 shows the β-coefficient of the peak in the model. A positive value of the coefficient β means that an increased peak height corresponds to increased risk of relapse.

TABLE 9

Most significant peaks, fdr = 0.6.

| Surface-Fraction | M/Z | Beta-coefficient |
|---|---|---|
| IMAC3-Fraction3 | 12139.4335 | 0.7736 |
| WCX2-Fraction2 | 11677.6762 | 0.168 |
| IMAC3-Fraction3 | 11483.9713 | 0.21 |
| IMAC3-Fraction3 | 11322.1079 | 0.416 |
| SAX2-Fraction2 | 11095.8768 | 3.9756 |
| WCX2-Fraction1 | 7831.326 | 0.3198 |
| IMAC3-Fraction4 | 11481.7153 | 0.1424 |
| IMAC3-Fraction3 | 12235.8865 | 1.0773 |
| WCX2-Fraction4 | 797.602 | 0.3471 |
| WCX2-Fraction4 | 783.9856 | 0.4367 |
| WCX2-Fraction2 | 11884.4738 | 0.7366 |
| WCX2-Fraction4 | 2507.8862 | 0.1917 |

Second Case: Using the Logarithm of the Peak Height to Fit the Cox Model.

In this case, f(Peak)=logPeak was utilized in the Cox model. FIG. 10 shows the BUM analysis of the 1976 p-values obtained after fitting the Cox models. It is evident that there are no significant peaks. In particular, the inventors have to set FDR >0.999 in order to get a p-value threshold that does not cut off all 1976 cases.

Example 3

Proteomic-Based Prediction of Clinical Behavior in Adult Acute Lymphoblastic Leukemia (ALL)

Despite the 90% long-term disease free survival that can be achieved in pediatric acute lymphoblastic leukemia (ALL), the long-term survival in adults with ALL remains poor. Only 30% to 40% of adults with ALL can expect a cure. Predicting adult patients who will relapse may help in devising a new therapeutic approach and perhaps allow initiation of therapy at an earlier stage.

Surface-enhanced laser desorption/ionization (SELDI) and the Ciphergen ProteinChip® system were used to study protein profiles in plasma from untreated patients with ALL to identify biomarkers that predict clinical behavior. Patients were randomly selected at the University of Texas M.D. Anderson Cancer Center among those with a diagnosis of ALL. Diagnosis was based on morphology, cytochemical staining, immunophenotypic analysis (CD34, CD64, CD13, CD33, CD14, CD117, CD10, CD19, CD3, CD20, DR, and TdT), and molecular analysis as indicated. Cytogenetic analysis was also performed. Informed consent was obtained and IRB-approved clinical research protocols were followed. The characteristics of the 57 patients in this study are listed in Table 10. Apparently healthy volunteers were used as controls for each chip.

TABLE 10

| | Median | Minimum | Maximum |
|---|---|---|---|
| AGE | 50 | 12 | 83 |
| B2M | 2.95 | 0 | 6.600 |
| WBC | 5.95 | .8 | 602.50 |
| PB BLAST % | 15 | 0 | 89 |
| PB Lymph % | 31.5 | 2.0 | 92.00 |
| PLT | 90.5 | 8.0 | 485.0 |
| HGB | 8.5 | 4.5 | 15.0 |
| BM BLAST % | 81.5 | 1.0 | 98.0 |
| BUN | 15 | 5 | 26 |
| CREAT | 0.9 | 0.5 | 2.7 |
| LDH | 898.5 | 285.0 | 22834.0 |

Samples were collected prior to initiation of cytotoxic therapy. EDTA plasma was obtained by centrifuging whole blood at 1500 g for 10 minutes at 4° C. Plasma was stored at −70° C. The plasma proteins were first fractionated based on their pH into four fractions using a strong anion exchange column as follows: pH 7+pH9+flowthrough, pH5, pH4, and pH3+organic wash. Each fraction was applied to three ProteinChip array surfaces: immobilized metal affinity capture (IMAC3), strong anion exchange (SAX2), and weak cation exchange (WCX2). Samples were divided into aliquots of two, and then randomly assigned to 8-well plates, with each plate containing a control from a pool of healthy patient samples.

Chips were read using the Ciphergen ProteinChip® Reader (series PBS II). Twenty-four spectra per patient (4 fractions×3 arrays in duplicate) were obtained. Peak detection was performed using CiphergenExpress 3.0 (Ciphergen Biosystems, Inc.). Spectra were normalized against total ion current between 2000 and 160,000 m/z. This software calculates clusters by determining peaks that are above a given signal-to-noise ratio, and that are present in multiple spectra. Various settings for noise subtraction, peak detection, and cluster completion were evaluated. The final settings chosen were similar to the vendor's default settings, a first pass peak detection of 5.0 signal-to-noise on both peaks and valleys, and a cluster completion window of 1.0 times peak width, with a second pass signal-to-noise setting of 2.0 for both peaks and valleys. Peaks were identified between 2000 and 200,000 m/z.

To compare automatic peak detection with manual peak detection, two of the 12 chip types were analyzed in depth (IMAC3 pH3 and WCX2 pH9). Peaks were detected manually, and then the results analyzed with Matlab (MathWorks, Natick, Mass.) followed by decision tree analysis using CART software implemented in Biomarker Patterns Software (Ciphergen Biosystems, Inc.). Minimal substantial differences were detected between manual peak identification and automatic peak identification and so automatic peak detection was used through the rest of the study.

An additional analysis was conducted to investigate various approaches through normalization to lower the inherent instrumental variability. Although the use of total ion current as a normalization factor is a common practice in SELDI data analysis, this limited normalization may not adequately eliminate other confounding changes common in mass spectrometry. It was hypothesized that ratios of peaks near each other were likely to be more reproducible than normalizing with total ion current alone. This peak ratio approach has an additional advantage of possibly detecting post-translational modifications more effectively (e.g. a percentage of a given concentration of peptides is phosphorylated, moving up +80 daltons to a different peak, and thus increasing the intensity of this peak at the expense of peak representing the non-phosphorylated peptide). For this reason, ratios of peaks within 5 peaks upstream and downstream of each peak were calculated, and these values were also included in the decision tree analysis.

To determine whether the use of ratios is likely to decrease or increase inherent variability, the following analysis was conducted. Peak values for each of the two patient replicates (aliquots with individual spectra) for all 117 peaks in the WCX2 pH9 fraction were read into Matlab. The CVs for each peak value between the replicates for each patient sample were recorded, along with the median CV for each peak. Then the overall median CV for all peaks was computed. Median CVs were used in the computation to restrict the effect of outliers. This process was repeated for eight other approaches: 2) dividing each peak by the total ion current in a spectrum; 3) dividing each peak by the mean peak intensity value over a spectrum; 4) calculating a ratio by dividing each peak by the closest neighbor; 5) a ratio by dividing each peak by its second closest neighbor to the right (higher m/z value); 6) dividing each peak by its third closest neighbor; 7) dividing each peak by its fourth closest neighbor, 8) dividing each peak by its fifth closest neighbor; and 9) dividing a peak by the average value of its closest 6 peak values (3 on each side).

For each of the 12 fraction types, the correlation matrix was calculated between all of the observational variables (clinical outcomes, patient demographics, and cellular analysis) and all peaks. A program was written in Matlab to plot the top 16 peaks with the lowest p value curve fitted to each observational variable within each fraction type. These plots were then manually inspected for correlation between the mass spec peaks and observational variables.

Decision tree algorithm (CART software from Salford Systems, implemented by Ciphergen in Biomarker Patterns Software 4.0) was used to identify peaks useful for prediction of responders and non-responders. The observational variables from cellular analysis were included as variables along with peak values and peak ratios of nearby neighbors (within 5 peaks above or below). When using decision trees, caution must be exercised to prevent overfitting (Wiemer and Prokudin 2004). To limit overfitting, only two levels were allowed, meaning that the model could only be comprised of at most two variables from the set of all peak values and all observational variables.

A total of 953 peaks were detected across the 12 fraction types. The number of peaks detected in each fraction type is shown in Table 11. The strongest predictors for relapse from all fractions are shown in Table 12.

TABLE 11

| Fraction Type | Number of Peaks |
|---|---|
| IMAC3/pH3 | 46 |
| IMAC3/pH4 | 50 |
| IMAC3/pH5 | 50 |
| IMAC3/pH9 | 57 |
| SAX2/pH3 | 96 |
| SAX2/pH4 | 99 |
| SAX2/pH5 | 97 |
| SAX2/pH9 | 80 |
| WCX2/pH3 | 94 |
| WCX2/pH4 | 82 |
| WCX2/pH5 | 87 |
| WCX2/pH9 | 115 |

TABLE 12

| Fraction type | p-value | m/z value |
|---|---|---|
| WCX2/pH9 | 5.31E-05 | 7727.972 |
| IMAC3/pH4 | 1.90E-04 | 61940.76 |
| SAX2/pH3 | 4.08E-04 | 124797.7 |
| WCX2/pH9 | 4.71E-04 | 53623.64 |
| WCX2/pH9 | 6.47E-04 | 10216.72 |
| SAX2/pH4 | 9.07E-04 | 145023.4 |
| SAX2/pH5 | 9.07E-04 | 6808.864 |
| WCX2/pH9 | 9.07E-04 | 7249.661 |
| WCX2/pH9 | 0.001030755 | 6588.005 |
| WCX2/pH9 | 0.001229988 | 78971.03 |
| WCX2/pH9 | 0.001697129 | 4924.562 |
| IMAC3/pH4 | 0.001724272 | 55864.83 |
| WCX2/pH9 | 0.001782018 | 6801.569 |
| WCX2/pH9 | 0.00182591 | 13298.19 |
| SAX2/pH3 | 0.002147563 | 83531.42 |
| WCX2/pH9 | 0.002435941 | 39542.43 |
| WCX2/pH9 | 0.002494388 | 159276.8 |
| SAX2/pH4 | 0.002735039 | 106256.1 |
| WCX2/pH9 | 0.002806334 | 88687.58 |
| IMAC3/pH9 | 0.003264825 | 135305.2 |

The median coefficient of variations for patient sample replicates from the WCX2 pH9 fraction using the various peak normalization approaches are shown in Table 13.

TABLE 13

| Normalization Approach | Median Coefficient of Variation (percent) |
|---|---|
| No normalization | 9.8 |
| Dividing by the total ion current in a spectrum | 11.5 |
| Dividing each peak by the mean peak intensity from all peaks in a spectrum | 10.2 |
| Calculating a ratio by dividing each peak by the next highest peak (closest neighbor) | 11.5 |
| Calculating a ratio by dividing each peak by the second closest neighbor | 12.5 |
| Calculating a ratio by dividing each peak by the third closest neighbor | 13.7 |
| Calculating a ratio by dividing each peak by the fourth closest neighbor | 14.0 |
| Calculating a ratio by dividing each peak by the fifth closest neighbor | 14.5 |
| Dividing each peak by the average value of its closest 6 peak neighbors (3 on each side) | 8.8 |

Using ratios of nearby peaks multiplies the number of possible variables, and caution should be taken when using this approach to avoid overfitting. However, a ratio approach can be useful in identifying biological affects that involve two peaks, for example a shift due to post-translational modification, or an alternative splice variant of a protein. With no normalization, the median coefficient of variation for repeated patient samples was 9.8 percent. The variation between replicates actually increased to 11.5 percent when dividing by the total ion current. Normalizing by dividing by the mean peak intensity from all peaks in a spectrum also slightly increased the variability. The only normalization approach that lowered variability was dividing by the mean of the closest six peaks. The replicate variability increased to between 10 and 14.5 percent when ratios are calculated using nearby peaks. The further away the peaks were in calculating the ratio, the greater the increase in the variation between replicates.

All patients except for 2 achieved response (96%). Thirteen of 55 (24%) relapsed at the time of analysis of these patients with median follow-up of 71 weeks (range 2-193 weeks). The majority of the patients (58%) were classified as L2 and 10% were classified as having L3 (Burkitt's).

In order to predict relapse, the correlation between relapse and the intensity of peaks of each of the 12 fraction/surface types was evaluated. The weak cation exchange (WCX2) at pH 9 had the greatest number of peaks and peak ratios at significant p-values (Table 11). Thirteen of the 20 peaks with the lowest p-values against the relapse status were from the WCX2 pH9 fraction.

Decision tree analysis was run first with all the peak values and then with nearby peak ratios. The decision tree also incorporated other laboratory characteristics including cytogenetics, WBC, percent of peripheral blood blasts, LDH, creatine, platelets, HGB, percent of lymphocytes, and beta-2 microglobulin. With a decision tree analysis of only two levels to limit overfitting, several models were generated. Three of these models are shown in FIGS. 11A-11C.

Figure 11A:
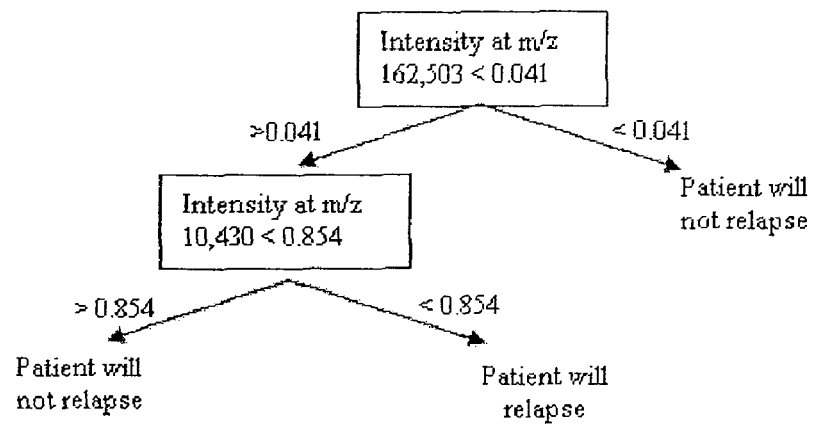
FIG. 11A-C: Three decision trees for predicting relapse in ALL patients.
Figure 11B:
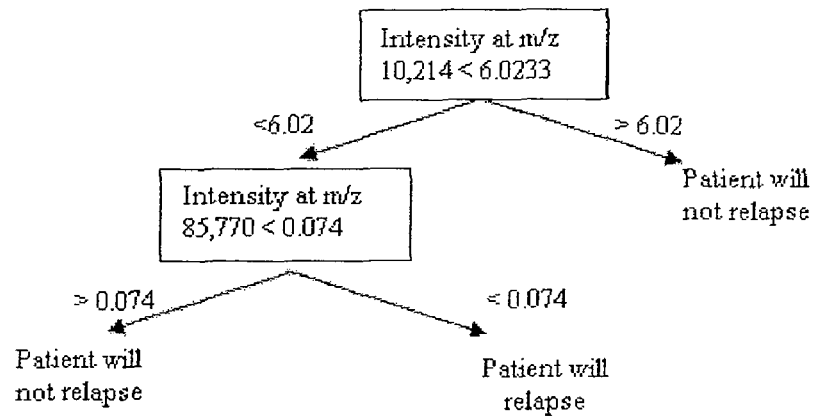
Figure 11C:
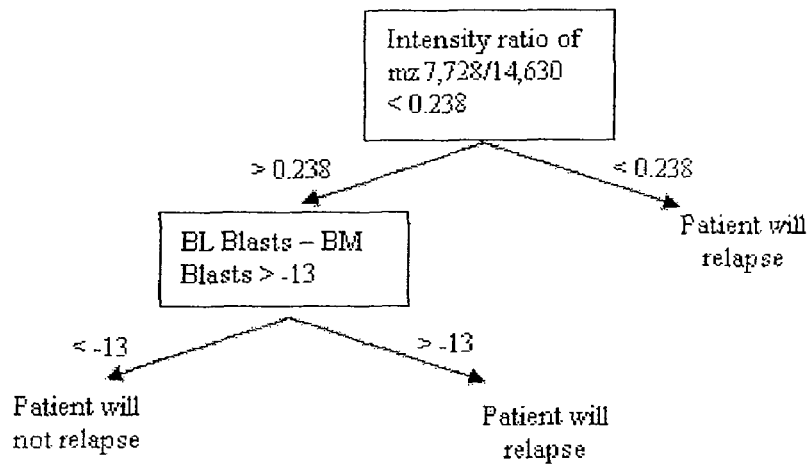

In the first model two peaks at m/z 162,503 and 10,430 of the WCX2 pH 9 fraction were able to predict relapse in a test set of 33% of the samples correctly in 92% of the cases (positive prediction) and the non-relapse (negative prediction) correctly in 72% of the cases (FIG. 11A). In the second model (FIG. 11B), using 33% of the cases as a test set positive prediction was 84% and negative prediction was 72% using two peaks of WCX2 pH 9 fraction at m/z 10,214 and 85,770. The third model was very strong in the positive prediction of relapse (92%), but weak in the negative prediction (FIG. 11C). This model used the relative ratio of two WCX2 pH 9 fraction peaks at 7728 and 14630 along with the percentage blasts in peripheral blood.

Figure 12:
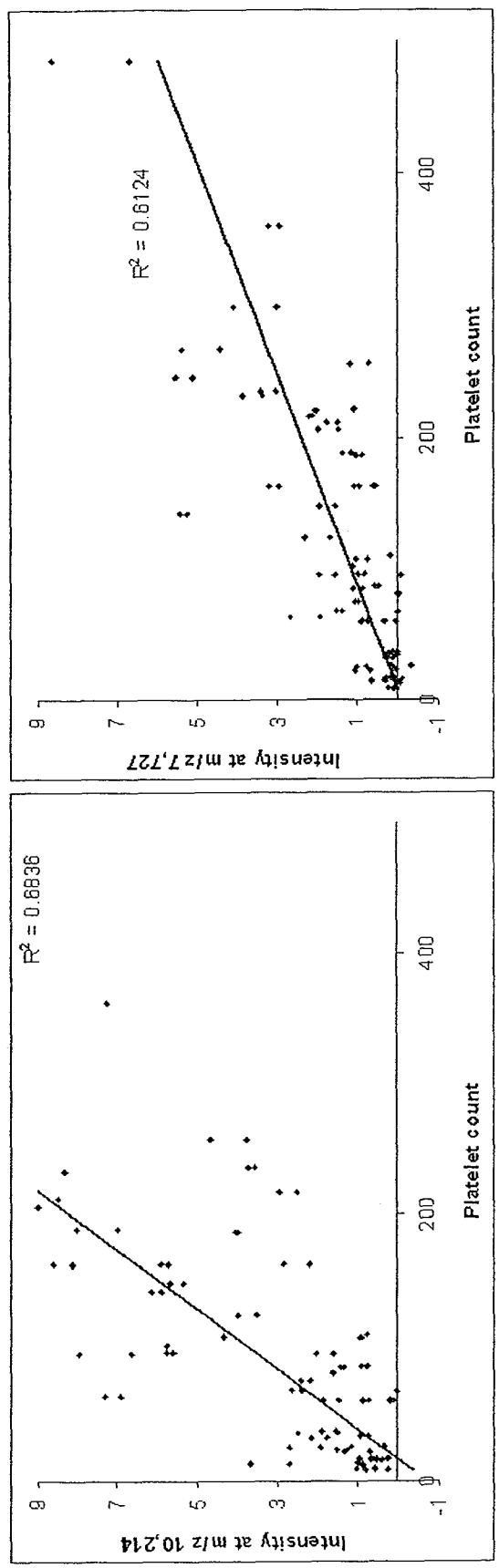
FIG. 12: Scatter plot between the peak intensity and platelet count of the two highest-correlated peaks with platelet count.

The presence of any correlation between the major laboratory information and the individual peak intensity was studied for all 12 fractions. This included WBC, HGB, creatin, LDH, and percents of blasts, lymphocytes, and monocytes in peripheral blood and bone marrow. There were very few strong correlations observed for the majority of the laboratory variables and the peaks or peak ratios. However, the platelet count was consistently well correlated with various peaks across all 12 fractions, with the strongest correlations in the WCX2 pH9 fraction. Out of 953 peaks across the 12 fraction types, there were 90 peaks that had better than a 0.001 p-value correlation with platelet count. Of these 953 peaks, Table 14 shows the 20 highest correlated peaks by p-value. FIG. 12 shows scatter plots between the peak intensity and the platelet count for the 2 highest correlated peak values.

TABLE 14

| Fraction Type | p-value | M/Z Value |
|---|---|---|
| WCX2/pH9 | 5.95E-12 | 7727.865343 |
| WCX2/pH9 | 9.98E-12 | 10214.09619 |
| IMAC3/pH5 | 2.61E-11 | 9263.336516 |
| IMAC3/pH9 | 3.49E-11 | 10217.12293 |
| IMAC3/pH9 | 1.28E-10 | 7722.657526 |
| WCX2/pH5 | 1.69E-10 | 7728.041349 |
| WCX2/pH9 | 4.79E-09 | 9268.979905 |
| IMAC3/pH5 | 5.94E-09 | 7741.020002 |
| WCX2/pH3 | 1.29E-08 | 9248.709422 |
| WCX2/pH3 | 3.51E-08 | 7720.190664 |
| SAX2/pH3 | 9.41E-08 | 13870.3916 |
| IMAC3/pH4 | 1.78E-07 | 7725.474001 |
| IMAC3/pH9 | 8.18E-07 | 9275.311795 |
| SAX2/pH4 | 8.63E-07 | 41782.2775 |
| WCX2/pH9 | 1.09E-06 | 8896.712054 |
| WCX2/pH3 | 1.29E-06 | 4911.78345 |
| SAX2/pH4 | 5.24E-06 | 83363.03733 |
| SAX2/pH4 | 5.28E-06 | 45087.95748 |

TABLE 14-continued

| Fraction Type | p-value | M/Z Value |
|---|---|---|
| SAX2/pH4 | 5.44E-06 | 121673.475 |
| IMAC3/pH3 | 6.27E-06 | 7727.155842 |

Figure 13:
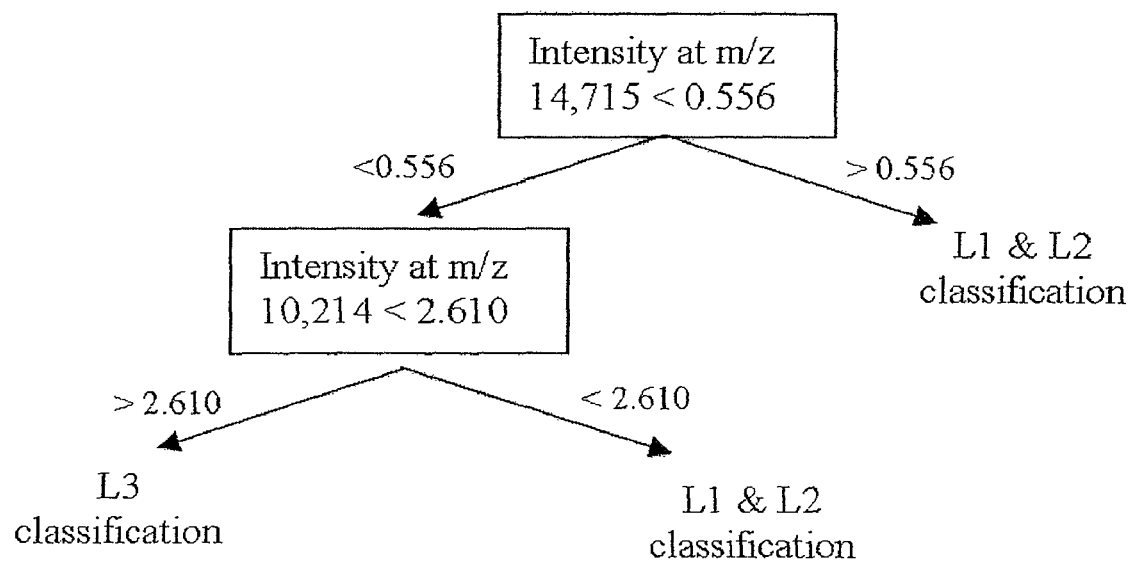
FIG. 13: A decision tree for predicting the L3 subtype in ALL patients.

As expected in adult ALL, the majority of the patients were classified based on morphology as L2 or L1 and only 10% as L3. Since distinguishing L1 from L2 is subjective and practically has no significant clinical value, L1 and L2 cases were considered together and compared with the L3 group. Distinguishing the L3 group is important due to their specific clinical course. Proteomics of peripheral blood plasma was used to identify specific peaks capable distinguishing the L1/L2 group from the L3 group. A model restricted to two peaks was developed using two WCX pH9 fractions at m/z 14,715 and 10,214 (FIG. 13). Using a test set (as V-fold cross validation), the inventors were able to positively predict the L1/L2 group in 94% and the L3 group in 80% of the cases. The data suggest that proteomic peaks could differentiate these two groups using decision tree analysis.

The data presented here support the use of peripheral blood plasma for proteomic analysis in leukemias and demonstrate that proteomic approach represents a valid approach for developing clinically useful biomarkers to be used in clinical management of patients with leukemia. The analysis also indicates a growing future role for the combination of mass spectrometry measured data with clinically observed variables in the prediction of disease progression.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the methods and compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,534,121
U.S. Pat. No. 6,398,933
Anderson and Anderson, *Molec. Cell. Proteom.*, 1(11):845-867, 2002.
Freifelder, In: *Physical Biochemistry Applications to Biochemistry and Molecular Biology*, 2nd Ed. Wm. Freeman and Co., NY, 1982.
Hanash et al., *Blood*, 73(2):527-532, 1989.
Hanash et al., *Proc. Natl. Acad. Sci. USA*, 83(3):807-811, 1986.
Voss et al., *Int. J. Cancer*, 91(2):180-186, 2001.
Wiemer, J. C. and A. Prokudin (2004). "Bioinformatics in proteomics: application, terminology, and pitfalls." Pathol Res Pract 200(2): 173-8.

What is claimed is:

1. A method of predicting an increased risk of relapse following therapy or distinguishing between L1/L2 and L3 in a patient with acute lymphoblastic leukemia (ALL) comprising:
   (a) performing mass spectrometry on a plasma sample from said patient to generate a protein spectra comprising protein peaks;
   (b) identifying a protein peak or group of protein peaks in the protein spectra corresponding to one or more of Peak 30 (7727.972 Daltons), Peak 31 (61940.76 Daltons), Peak 32 (124797.7 Daltons), Peak 33 (53623.64 Daltons), Peak 34 (10216.72 Daltons), Peak 35 (145023.4 Daltons), Peak 36 (6808.864 Daltons), Peak 37 (7249.661 Daltons), Peak 38 (6588.005 Daltons), Peak 39 (78971.03 Daltons), Peak 40 (4924.562 Daltons), Peak 41 (55864.83 Daltons), Peak 42 (6801.569 Daltons), Peak 43 (13298.19 Daltons), Peak 44 (83531.42 Daltons), Peak 45 (39542.43 Daltons), Peak 46 (159276.8 Daltons), Peak 47 (106256.1 Daltons), Peak 48 (88687.58 Daltons), Peak 49 (135305.2 Daltons), Peak 50 (7727.865343 Daltons), Peak 51 (10214.09619 Daltons), Peak 52 (9263.336516 Daltons), Peak 53 (10217.12293 Daltons), Peak 54 (7722.657526 Daltons), Peak 55 (7728.041349 Daltons), Peak 56 (9268.979905 Daltons), Peak 57 (7741.020002 Daltons), Peak 58 (9248.709422 Daltons), Peak 59 (7720.190664 Daltons), Peak 60 (13870.3916 Daltons), Peak 61 (7725.474001 Daltons), Peak 62 (9275.311795 Daltons), Peak 63 (41782.2775 Daltons), Peak 64 (8896.712054 Daltons), Peak 65 (4911.78345 Daltons), Peak 66 (83363.03733 Daltons), Peak 67 (45087.95748 Daltons), Peak 68 (121673.475 Daltons), or Peak 69 (7727.155842 Daltons), and
   (c) predicting risk of relapse following therapy or distinguishing between L1/L2 and L3 based on the identification of one or more of Peaks 30-69, wherein Peaks 30-49 are predictive of an increased risk of relapse following therapy, and Peaks 50-69 distinguish between L1/L2 and L3 ALL.

2. The method of claim 1, wherein the mass spectrometry is surface-enhanced laser desorption/ionization (SELDI) mass spectrometry.

3. The method of claim 1, further comprising correlating clinical data from the patient with the one or more spectral peaks for predicting whether the patient will relapse.

4. The method of claim 3, wherein the clinical data comprises one or more of cytogenetics, age, performance status, response to therapy, time from response to relapse, and survival time.

* * * * *